(12) United States Patent
Bonadio et al.

(10) Patent No.: US 11,134,969 B2
(45) Date of Patent: Oct. 5, 2021

(54) TENACULUM

(71) Applicant: ATROPOS LIMITED, Bray (IE)

(72) Inventors: Frank Bonadio, Bray (IE); Stephen Williams, Blackrock (IE); Shane J. McNally, Edengate (IE); Ronan B. McManus, Bray (IE); Debora La Bella, Bray (IE); Lucy Dolores Halpin, Rathfarnham (IE)

(73) Assignee: ATROPOS LIMITED, Bray (IE)

(*) Notice: Subject to any disclaimer, the term of this patent is extended or adjusted under 35 U.S.C. 154(b) by 156 days.

(21) Appl. No.: 15/758,267

(22) PCT Filed: Sep. 8, 2016

(86) PCT No.: PCT/EP2016/071229
§ 371 (c)(1),
(2) Date: Mar. 7, 2018

(87) PCT Pub. No.: WO2017/042294
PCT Pub. Date: Mar. 16, 2017

(65) Prior Publication Data
US 2018/0256181 A1 Sep. 13, 2018

Related U.S. Application Data

(60) Provisional application No. 62/217,319, filed on Sep. 11, 2015.

(30) Foreign Application Priority Data

Sep. 29, 2015 (EP) ..................... 15187338
Jul. 4, 2016 (EP) ..................... 16177849

(51) Int. Cl.
*A61B 17/28* (2006.01)
*A61B 17/29* (2006.01)
*A61B 90/00* (2016.01)
*A61B 17/00* (2006.01)

(52) U.S. Cl.
CPC ............ *A61B 17/282* (2013.01); *A61B 17/29* (2013.01); *A61B 90/08* (2016.02);
(Continued)

(58) Field of Classification Search
CPC .................. A61B 17/282; A61B 17/29; A61B 2017/00287; A61B 2017/00358;
(Continued)

(56) References Cited

U.S. PATENT DOCUMENTS 2,743,726 A  5/1956 Grieshaber
3,779,248 A  12/1973 Karman
(Continued)

*Primary Examiner* — Kathleen S Holwerda
*Assistant Examiner* — Brooke Labranche
(74) *Attorney, Agent, or Firm* — Bookoff McAndrews, PLLC

(57) ABSTRACT

An instrument such as a tenaculum comprises a pair of jaws (202, 203) which are pivotal from an open configuration in which the jaws (202, 203) are splayed apart to a closed low profile delivery configuration. The jaws (202, 203) each have tissue engagement features (201). A protector loop (200) for each jaw which may be of a shape memory material such as Nitinol provides a safety protective distal tip which is distal of the tissue engaging features (201). The atraumatic tip does not harm tissue and does not compromise the integrity of a bag which may be used as a containment device in a procedure such as a hysterectomy.

20 Claims, 25 Drawing Sheets

(52) U.S. Cl.
CPC ........... *A61B 2017/00287* (2013.01); *A61B 2017/00358* (2013.01); *A61B 2017/00477* (2013.01); *A61B 2017/00867* (2013.01); *A61B 2017/2829* (2013.01); *A61B 2017/2926* (2013.01); *A61B 2090/0801* (2016.02); *A61B 2090/08021* (2016.02)

(58) Field of Classification Search
CPC ........... A61B 2017/00477; A61B 2017/00867; A61B 2017/2829; A61B 2017/2926; A61B 2090/0801; A61B 2090/08021; A61B 90/08; A61B 17/42; A61B 17/4241; A61B 17/30; A61B 17/3421; A61B 2017/4225; A61B 2017/00336; A61B 1/303; A61B 1/31; A61B 1/32; A61D 1/08; A45D 26/0066
See application file for complete search history.

(56) References Cited

U.S. PATENT DOCUMENTS

| | | | |
|---|---|---|---|
| 4,834,090 A | | 5/1989 | Moore |
| 5,059,198 A | * | 10/1991 | Gimpelson .......... A61B 17/282 |
| | | | 606/119 |
| 5,250,072 A | * | 10/1993 | Jain ...................... A61B 17/282 |
| | | | 606/205 |
| 5,584,855 A | | 12/1996 | Onik |
| 2004/0097961 A1 | * | 5/2004 | Burbank ................ A61B 17/42 |
| | | | 606/119 |
| 2006/0106109 A1 | * | 5/2006 | Burbank ................ A61B 17/12 |
| | | | 514/561 |
| 2008/0262539 A1 | | 10/2008 | Ewers et al. |
| 2012/0101518 A1 | | 4/2012 | DePond |
| 2015/0032119 A1 | * | 1/2015 | Kuroda ................ A61B 17/295 |
| | | | 606/113 |

\* cited by examiner

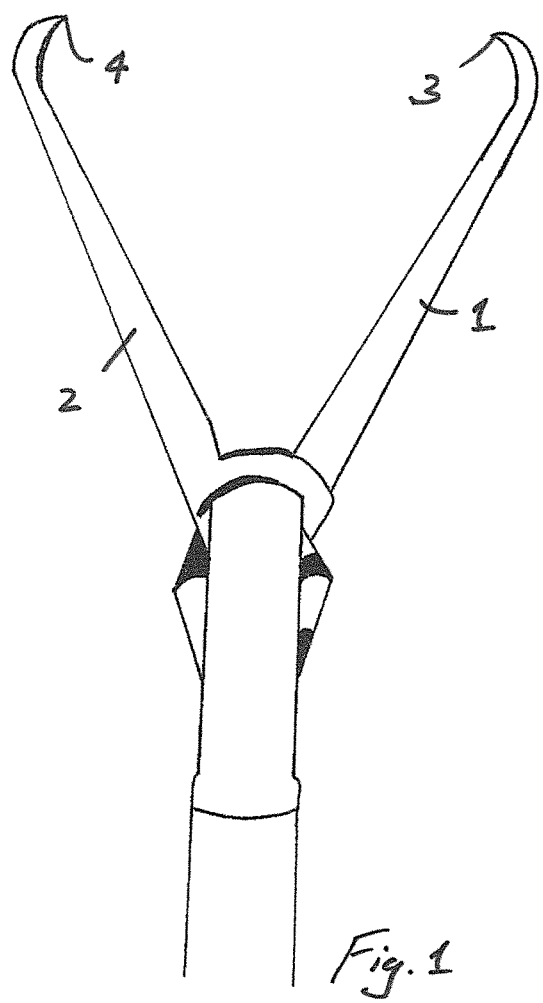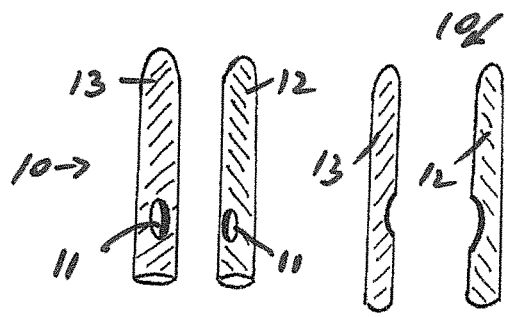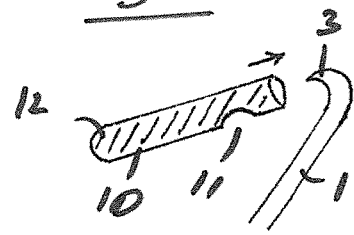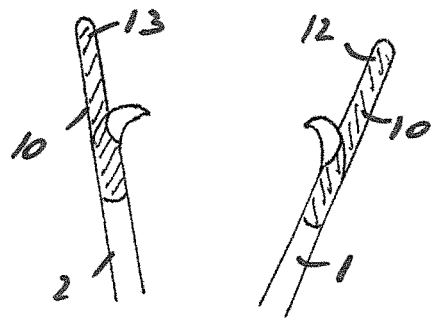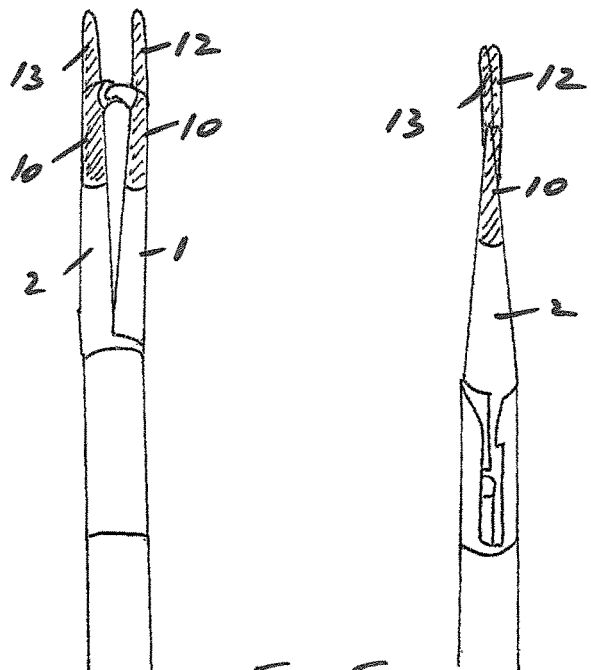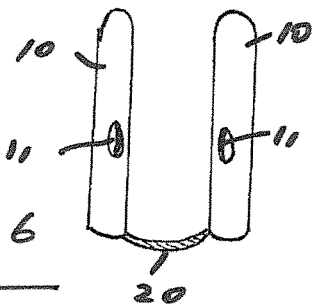

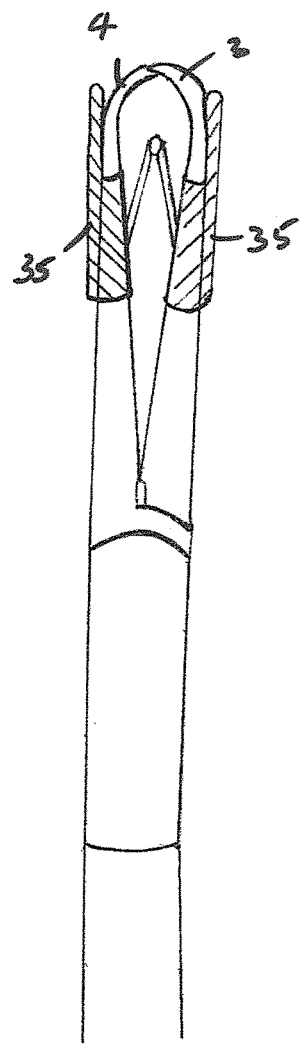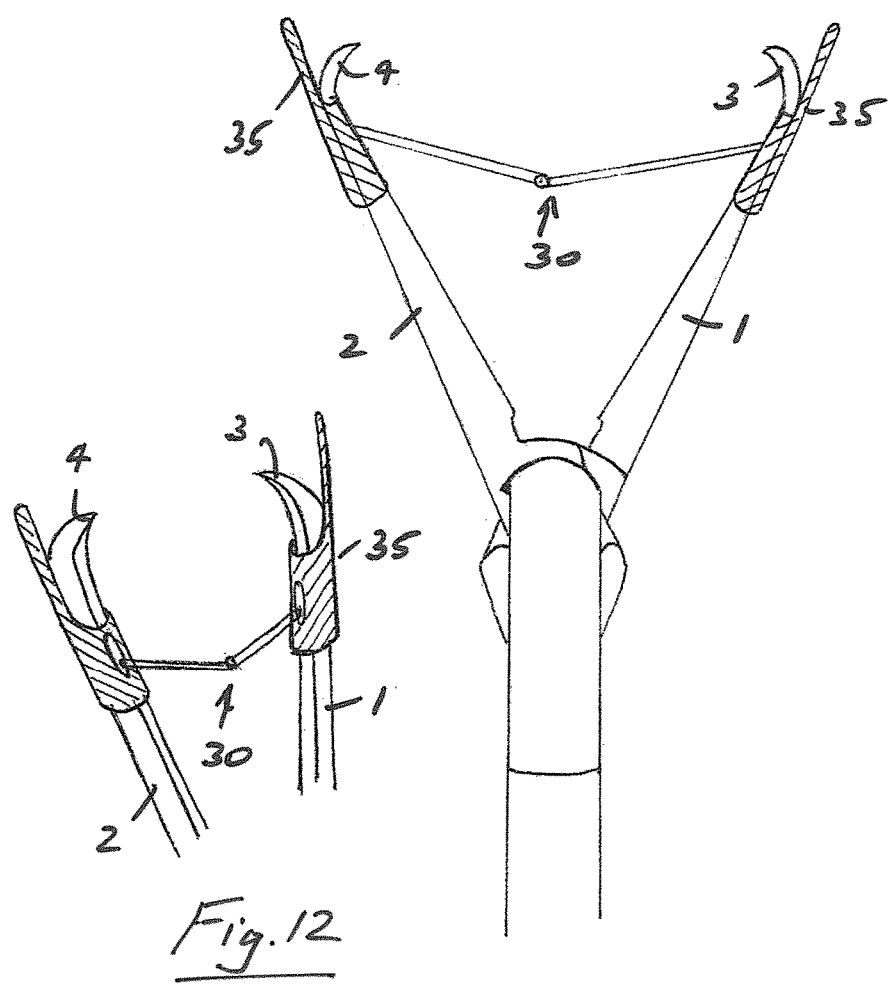
Fig. 11  Fig. 12  Fig. 13

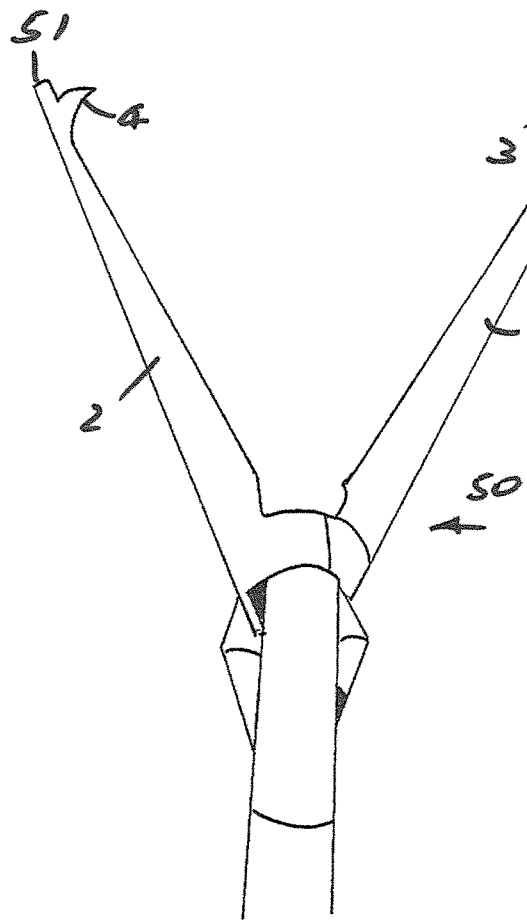
Fig. 20
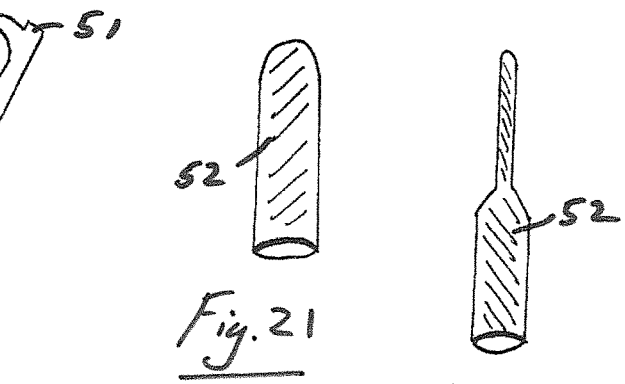
Fig. 21  Fig. 23
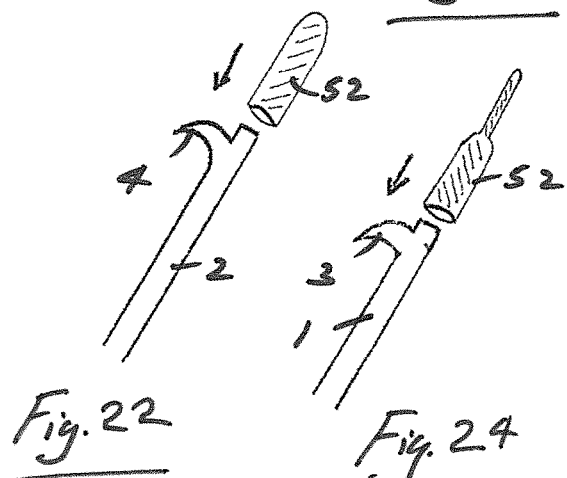
Fig. 22  Fig. 24
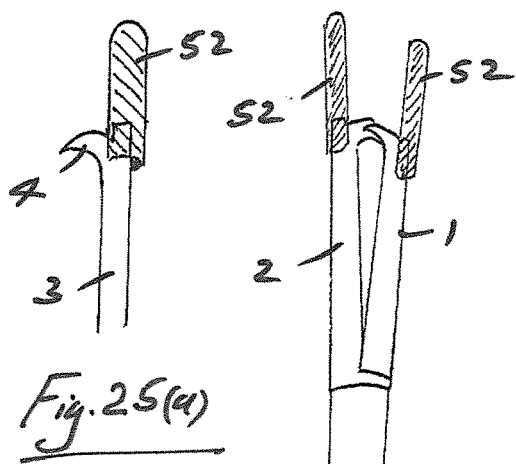
Fig. 25(a)
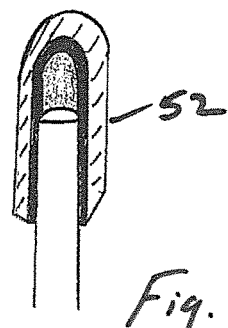
Fig. 25(b)
Fig. 26

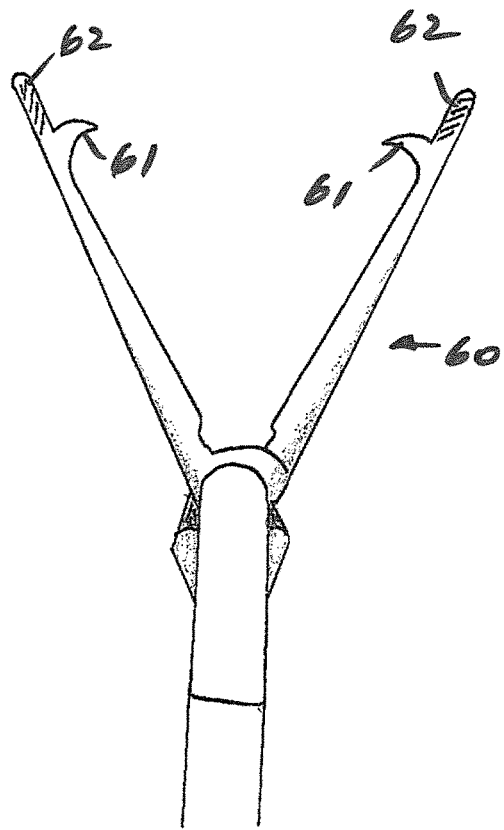
Fig. 27
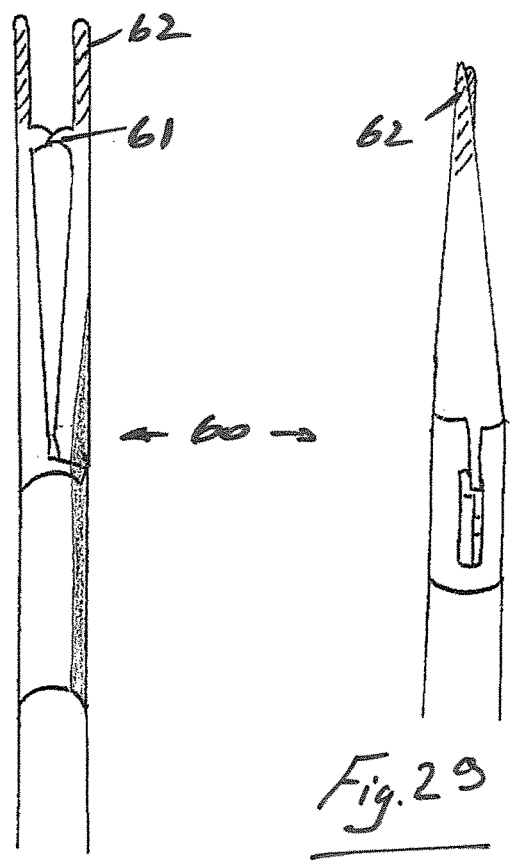
Fig. 28
Fig. 29
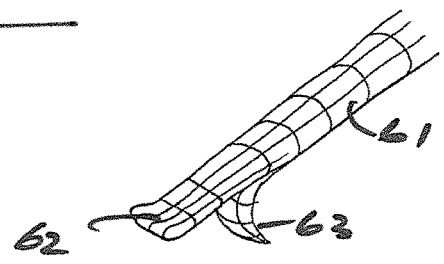
Fig. 30
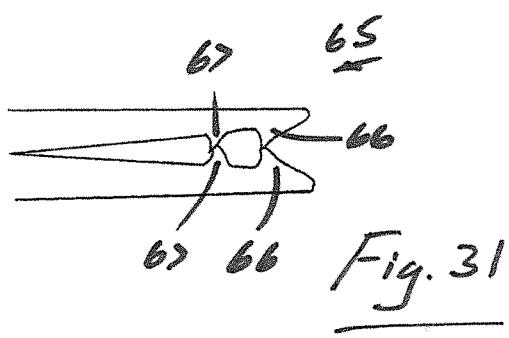
Fig. 31

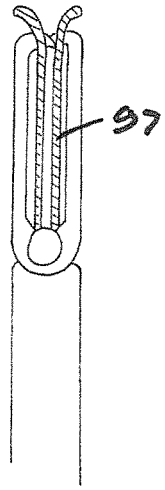
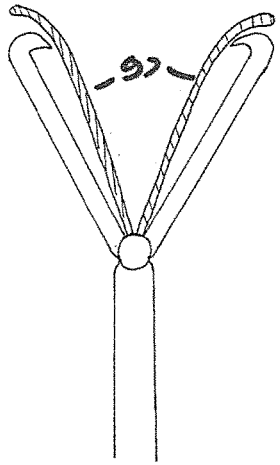
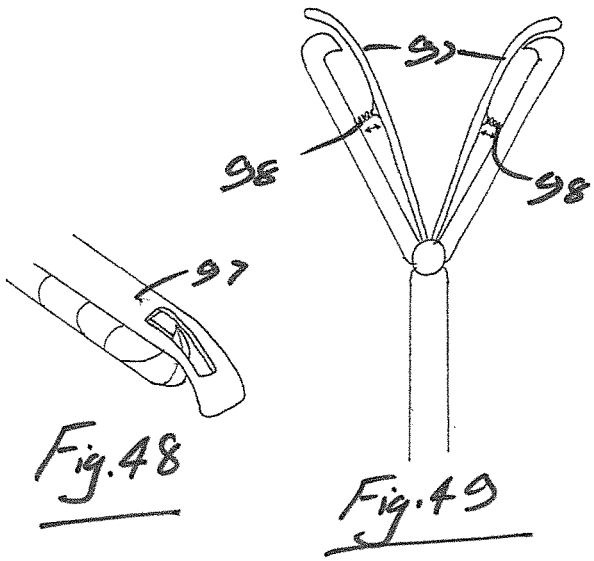
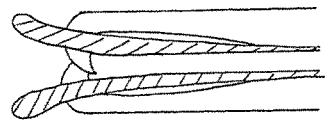
Fig. 46  Fig. 47  Fig. 48  Fig. 49
Fig. 50
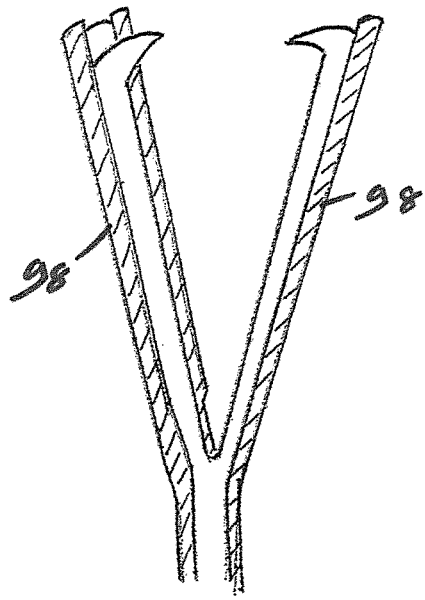
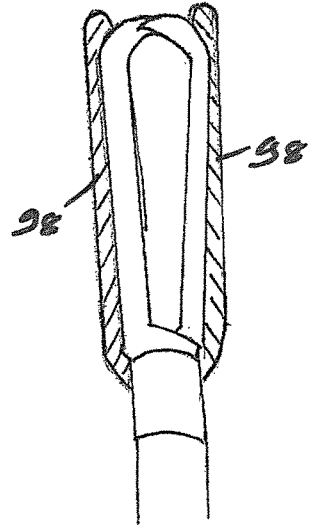
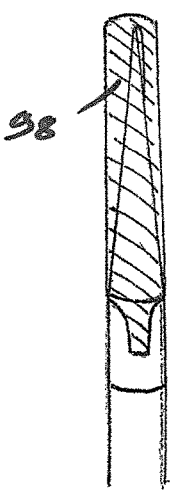
Fig. 51  Fig. 52  Fig. 53

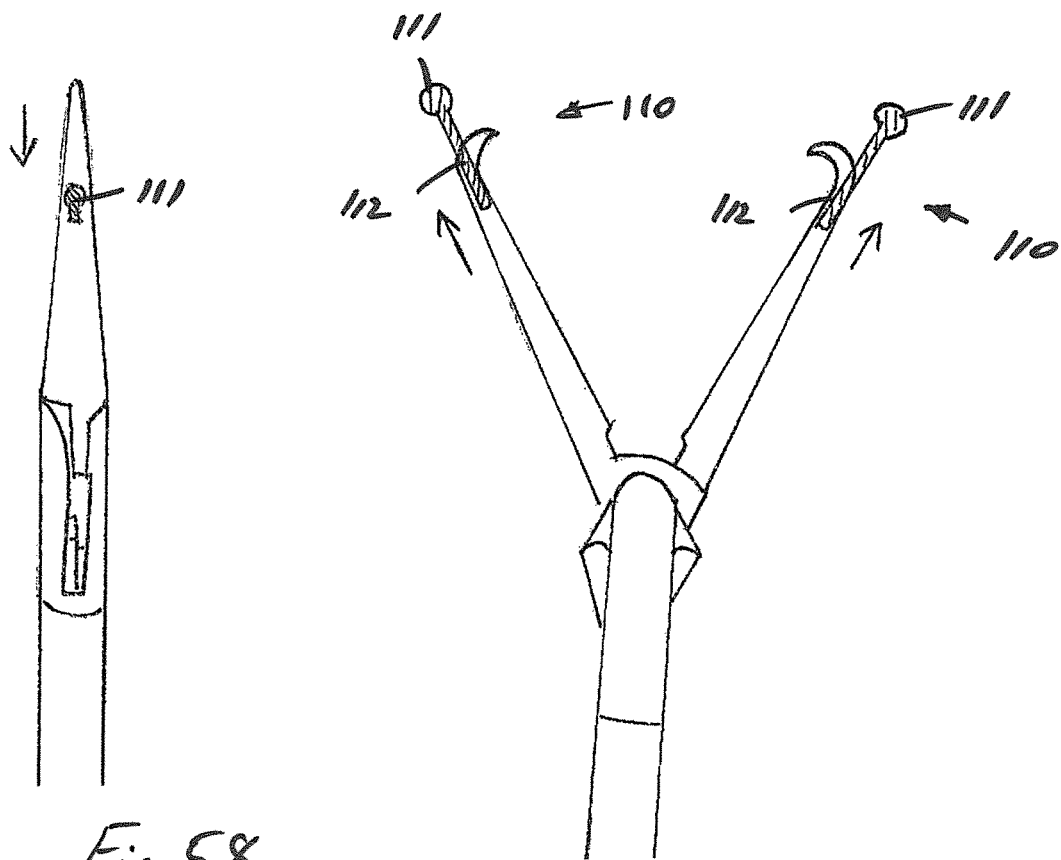
Fig. 58
Fig. 59
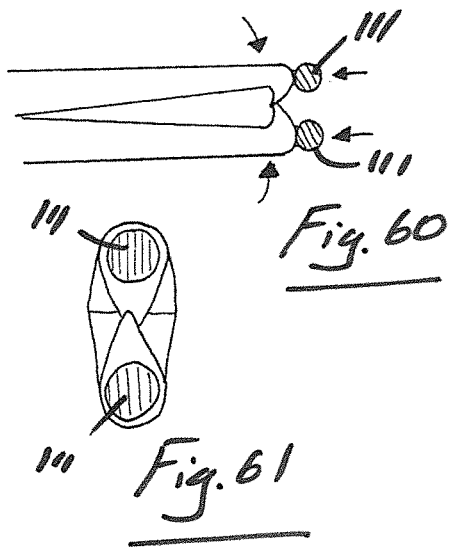
Fig. 60
Fig. 61
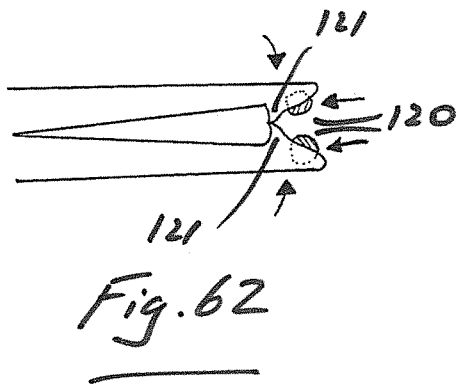
Fig. 62

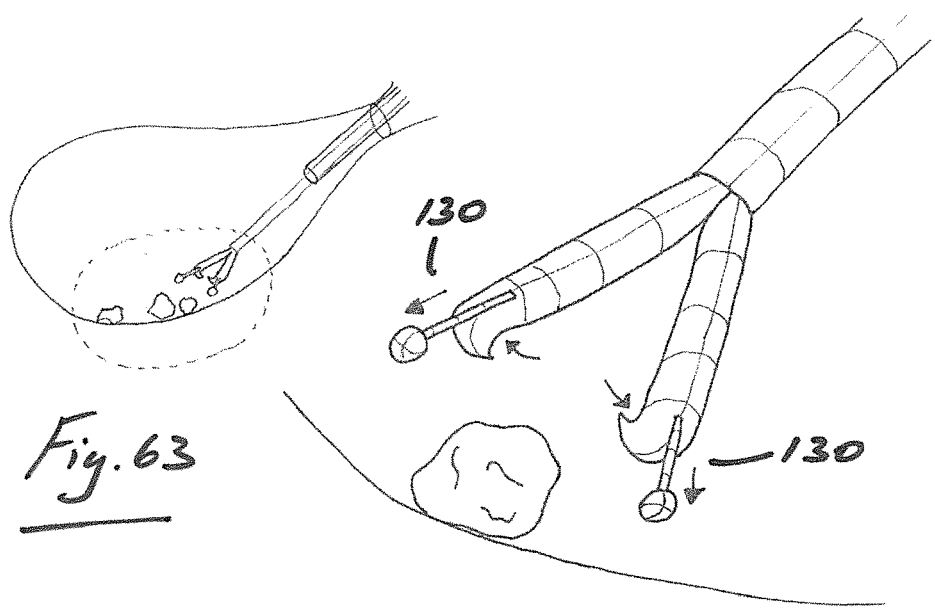
Fig. 63
Fig. 64
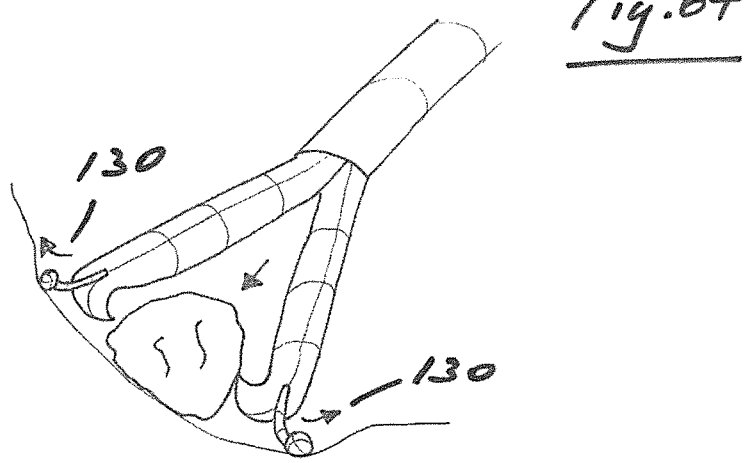
Fig. 65
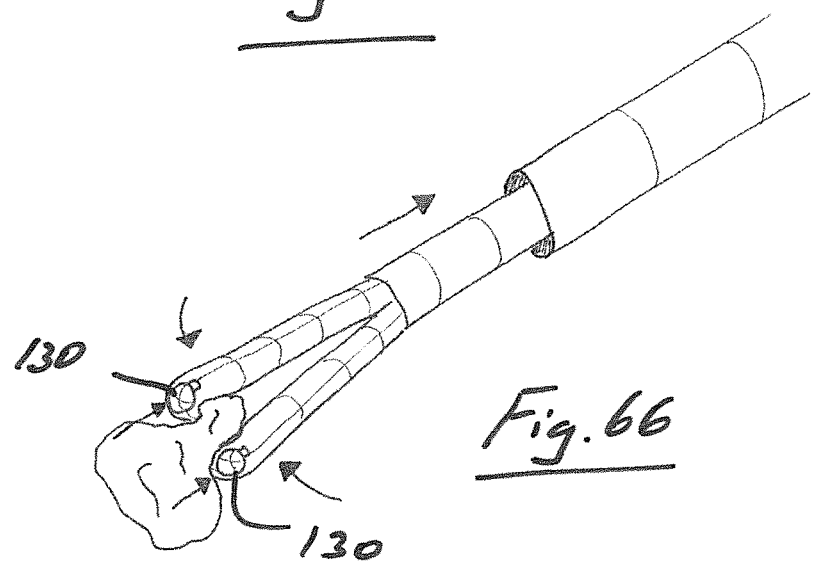
Fig. 66

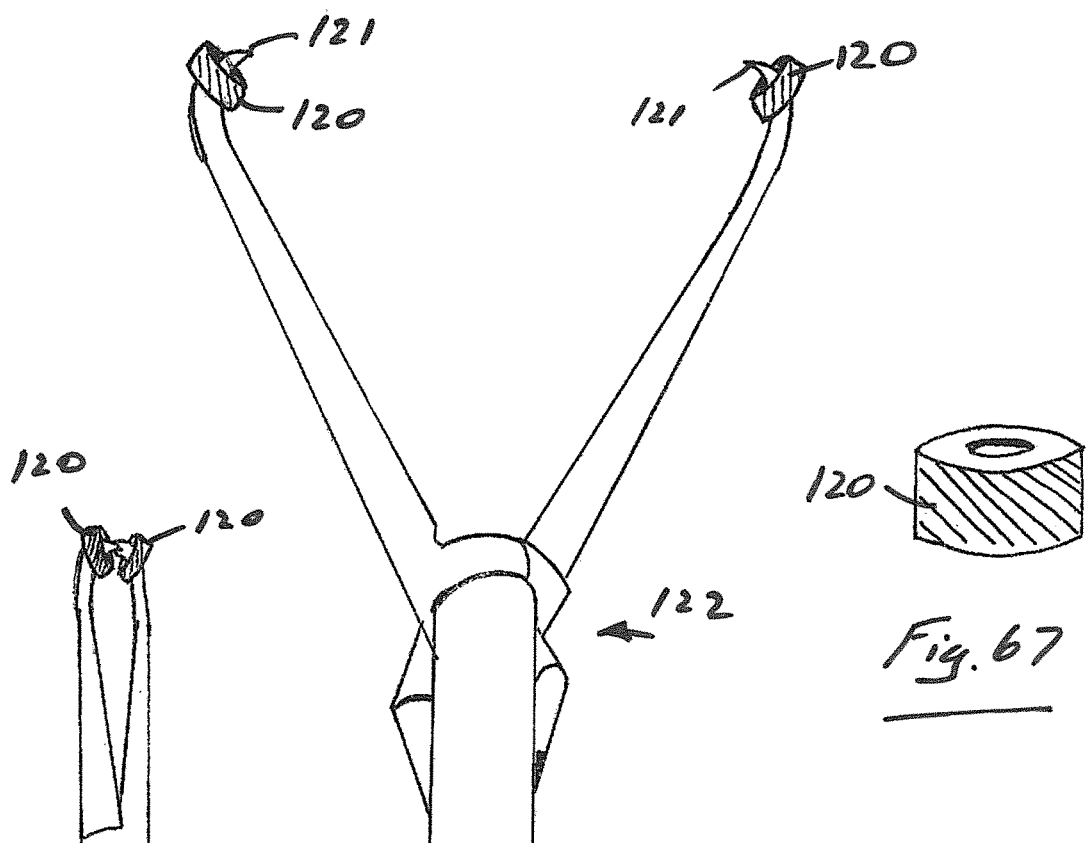
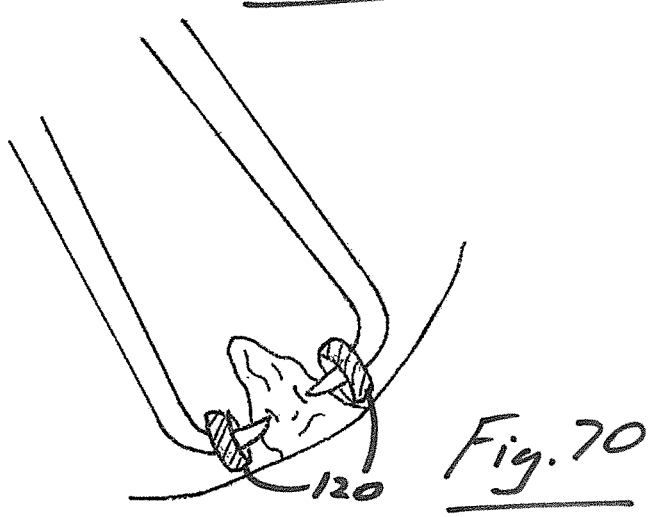
Fig. 67
Fig. 68
Fig. 69
Fig. 70

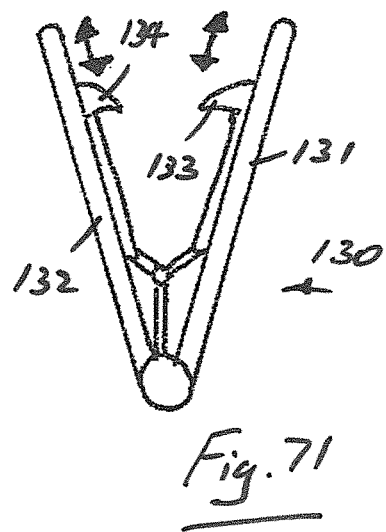
Fig. 71
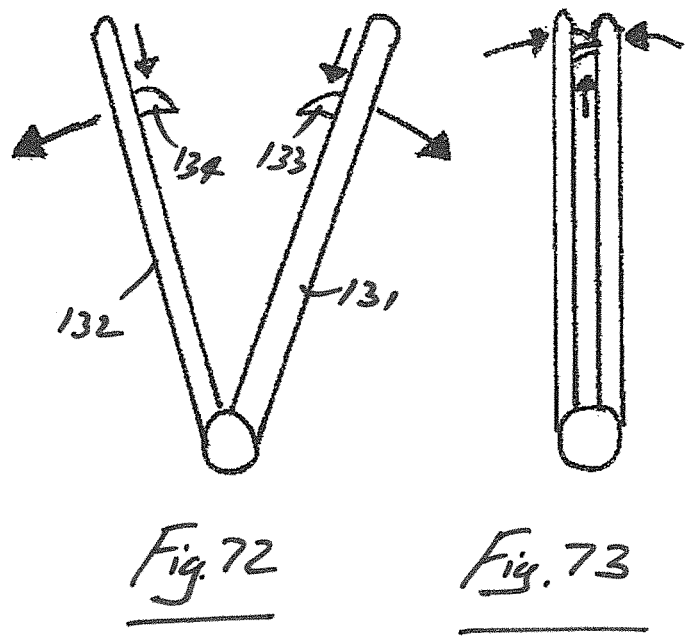
Fig. 72
Fig. 73
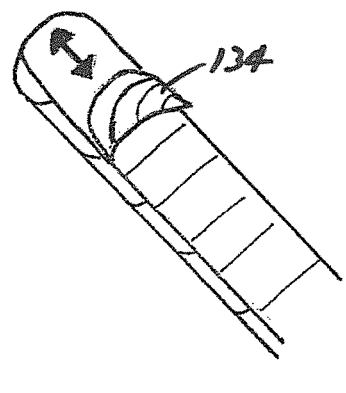
Fig. 74
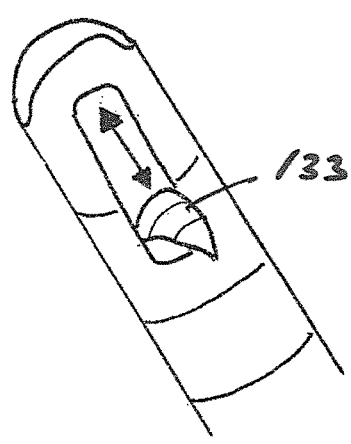
Fig. 75

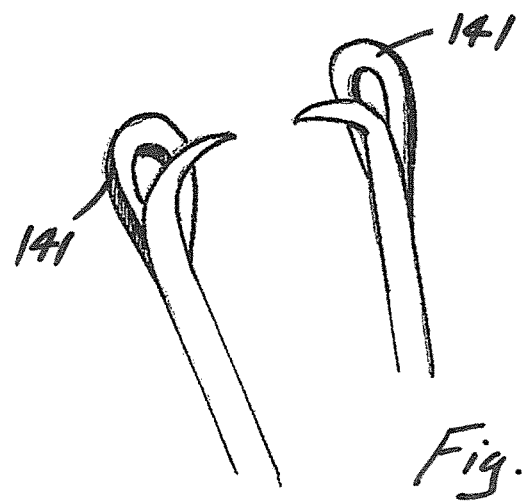
Fig. 76
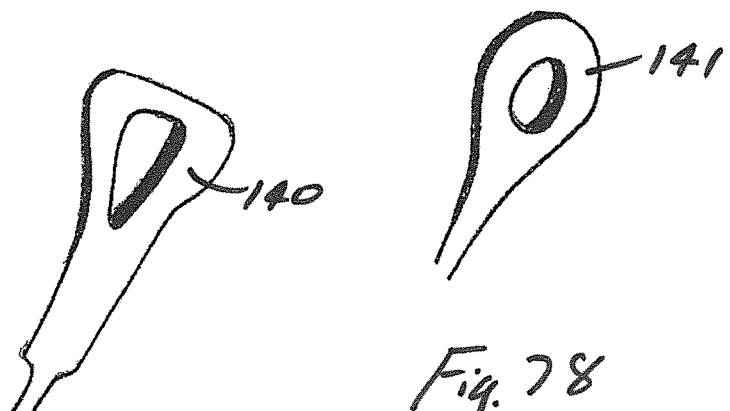
Fig. 77
Fig. 78

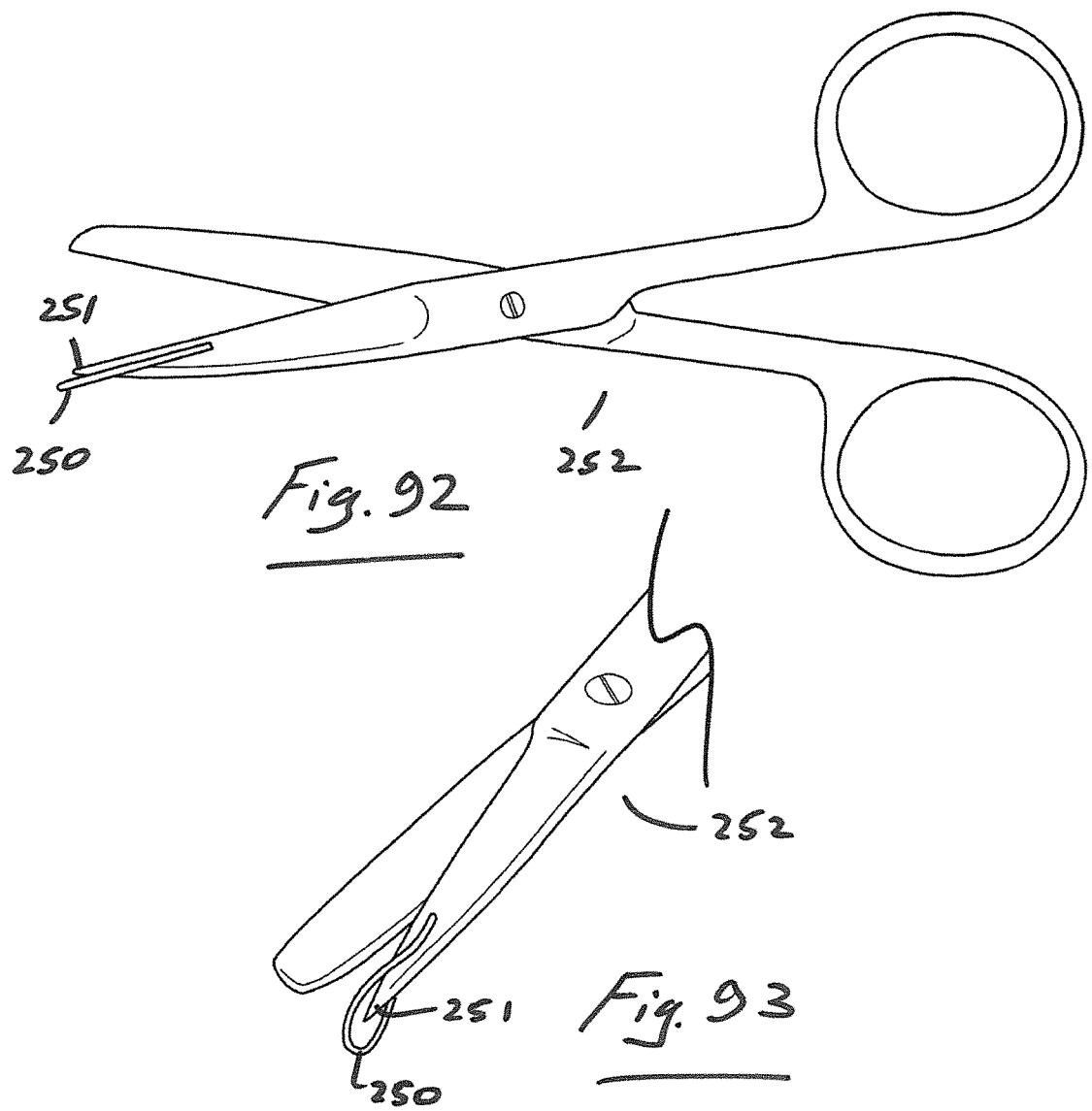

TENACULUM

CROSS-REFERENCE TO RELATED APPLICATIONS

This patent application is a U.S. national phase entry under 35 U.S.C. § 371 of International Application No. PCT/EP2016/071229, filed Sep. 8, 2016, which claims the benefit under 35 U.S.C. § 119 to U.S. Provisional Patent Application No. 62/217,319, filed on Sep. 11, 2015, European Application No. 15187338.7, filed Sep. 29, 2015, and European Application No. 16177849.3, filed Jul. 4, 2016, the entireties of which are incorporated herein by reference.

INTRODUCTION

This invention relates general to the field of instruments, especially for use in minimally invasive surgery.

Some laparoscopic procedures such as hysterectomies require tissue to be manipulated and removed through a small incision or natural body orifice. Such procedures may involve tissue morcellation.

Various instruments are used during such procedures, for example to grasp and/or manipulate tissue. Such instruments often include a pointed or sharp feature such as a tissue engagement feature. Such features, especially engagement features pose a risk in use of injuring tissue and/or of puncturing a containment bag in which the tissue is housed during the procedure, thus compromising the containment of tissue in the bag.

Such instruments generally have a pair of jaws that are connected at a common pivot. Finger rings or handles are usually provided at the end of one or both legs to allow an operator such as a surgeon to manipulate the instrument. Examples of such instruments include a forceps, a grasper or scissors. One such instrument is a tenaculum which has tissue engagement features such as spikes at the distal end of one or both jaws to facilitate a firm engagement with tissue.

The invention is directed towards providing an improved instrument such as a tenaculum which will address at least some of the problems with conventional instruments.

STATEMENTS OF INVENTION

According to the invention there is provided an instrument such as a tenaculum comprising:
  a first jaw and second jaw, the first jaw being pivotally movable relative to the second jaw,
  at least the first jaw having a pointed or sharp feature such as a tissue engaging feature at or adjacent to a distal end thereof; and
  a first protective element extending rom or extendable from the distal end of the first jaw to provide a protective distal tip which extends distally of the pointed or sharp feature.

In one embodiment the second jaw has a pointed or sharp feature at or adjacent to a distal end thereof, and a second protective element extends from or is extendable from the distal end of the second jaw to provide a protective distal tip which extends distally of the pointed or sharp feature.

In one case the first and the second jaws are pivotally movable relative to each other.

In one embodiment the or each protector element comprises a loop which extends around the engagement tip of the pointed or sharp engaging feature.

In one embodiment the loop circumscribes the tissue engaging feature.

The loop may be a wire loop. The loop may comprise a shape memory material such as Nitinol.

In one embodiment the loop extends distally of the distal tip of the jaws.

In some embodiments the loop is movable.

The loop may be retractable proximally from an extended configuration in which the loop extends distally of the distal tip of the jaw to a retracted configuration.

In one case the or each jaw comprises a tissue engaging feature at the distal end of the jaw.

In some cases the or each jaw comprises a plurality of tissue engaging features at the distal end of the jaws.

The invention also provides an instrument comprising:
  a first jaw having a tissue engaging feature at the distal end of the first jaw, a first protector loop extending around the tip of the tissue engaging feature of the first jaw; and a second jaw having a tissue engaging feature at the distal end of the second jaw, a second protector loop extending around the tip of the tissue engaging feature of the second jaw.

In one embodiment the first protector loop extends distally of the first jaw and the second protector loop extends distally of the second jaw and the distal portions of the first and second loops are configured to define a grasper.

In some embodiments the or each protector loop is movable from a distally extended configuration to a more proximal configuration.

The invention also provides an instrument comprising:
  a pair of jaws which are pivotally movable relative to one another, at least one jaw having a pointed or sharp feature such as a tissue engaging feature at or adjacent to the distal end thereof; and
  a protector element extending from or extendable from the distal end of the jaw to provide a protective distal tip which is distal of the feature.

The invention also provides and instrument comprising:
  a pair of jaws, at least one of the jaws being pivotally movable relative to the other jaw, at least one jaw having a pointed or sharp feature such as a tissue engaging feature at or adjacent to a distal end thereof; and
  a protective element extending from or extendable from the distal end of the jaw to provide a protective distal tip which is distal of the pointed or sharp feature.

In one aspect the protector element is releasably mounted to the jaw.

The protector element may comprise a hole through which the engagement feature of the jaw projects.

In one case the protector element is frictionally engaged with the distal end of the jaw. The protector element may be an interference fit with the distal end of the jaw.

In some cases the protector element is movable from a retracted configuration when the jaws of the instrument are closed to an extended protective configuration when the jaws of the instrument are open.

In one embodiment a connector extends between the protector elements. The connector may include at least one joint to facilitate movement of the protector elements between the retracted and extended configurations. The connector may comprise a tether which may be flexible, in one case the tether is integral with the protector element.

In one embodiment the jaw is adapted to or configured for mounting of the protector element to the jaw. The jaw and/or the protector element may comprise a mounting feature for mounting of the protector element to the jaw, the mounting feature may for example comprise a twist lock or a snap fit.

In one embodiment each of the jaws comprises a tissue engagement feature and wherein the tissue engagement features are movable from an extended position near the distal tip of the jaws when the jaws are closed to a retracted position more proximal of the distal tip when the jaws open, the distal end of jaws being extended or extendable beyond the tissue engaging features to provide a protective atraumatic distal tip.

The jaws may comprise a protector portion which is movable from a retracted configuration to an extended configuration.

In one case the jaw has an inner surface, from which the engaging feature projects inwards, and an outer surface, the protector may extend at least in part around a portion of the outer surface of the jaw, and/or the protector extends at least in part around a portion of the inner surface of the jaw, and/or the protector extends only around a portion of the inner surface of the jaw.

At least a portion of the protector may be spaced inwardly from the inner surface of the jaw, the protector may substantially enclose the tissue engaging feature of the jaw when the jaw is in a closed position.

In some embodiments the protector comprises a shape memory material such as Nitinol.

In some cases the protector comprises a loop which extends over the distal tip of the tissue engaging feature. The loop may define a shaped distal tip which may be rounded.

In some cases the protector comprises a wire loop.

In some embodiments a loop extends distally of the distal tip of each jaw to define a grasper.

In one embodiment the protector is movable from a protective configuration extending distal of the tissue engaging feature of a jaw to a retracted configuration in which the tissue engaging feature is exposed. The protector may be biased into the protective configuration. The biasing may comprise a spring. The protector may be adapted to move into the retracted configuration as the jaws move towards one another.

In some embodiments the protector is integral with the jaw.

In one case the protector has a profile in the shape of a fin.

According to the invention there is provided a tenaculum comprising:
 a pair of jaws which are pivotally movable relative to one another, each jaw having a tissue engaging feature at or adjacent to the distal end thereof; and
 a protector element extending from or extendable from the distal end of at least one of the jaws to provide a protective distal tip which is distal of the tissue engaging features.

The invention also provides a protector element for a tenaculum.

In one case the protector element is releasably mounted to the tenaculum jaw.

The protector element may comprise a hole through which the engagement feature of the tenaculum jaw projects.

In one case the protector element is frictionally engaged with the distal end of the tenaculum jaw.

The protector element may be an interference fit with the distal end of the tenaculum jaw.

In one embodiment the protector element extends or is extendable distally from the distal end of the tenaculum jaw.

The protector element may comprise a sleeve portion for engagement with the tenaculum jaw.

In one case the protector element is movable from a retracted configuration when the jaws of the tenaculum are closed to an extended protective configuration when the jaws of the tenaculum are open. A connector may extend between the protector elements. The connector may include at least one joint to facilitate movement of the protector elements between the retracted and extended configurations.

In one embodiment a connector extends between the protector elements of the tenaculum jaws. The connector may comprise a tether which may be flexible. The tether may be integral with the protector element.

In one embodiment the jaw of the tenaculum is adapted to or configured for mounting of the protector element to the jaw. The jaw and/or the protector element may comprise a mounting feature for mounting of the protector element to the jaw. The mounting feature may comprise a twist lock, or a snap fit, for example.

The invention also provides a tenaculum comprising a pair of jaws which are pivotally movable relative to one another, each jaw having a tissue engaging feature adjacent to the distal end of the jaw wherein the distal end of the jaws provide a protective atraumatic tip.

The invention also provides a tenaculum wherein each of the jaws comprises a tissue engagement feature and wherein the tissue engagement features are movable from an extended position near the distal tip of the jaws when the jaws of the tenaculum are closed to a retracted position more proximal of the distal tip when the jaws open.

In one case the distal end of jaws are extended or extendable beyond the tissue engaging features to provide the protective atraumatic tip.

In one embodiment the jaws comprise a protector portion which is movable from a retracted configuration to an extended configuration.

In one case the tenaculum jaw has an inner surface, from which the engaging feature projects inwards, and an outer surface. The protector may extend at least in part around a portion of the outer surface of the jaw. The protector may extend at least in part around a portion of the inner surface of the jaw. The protector may extend only around a portion of the inner surface of the jaw.

In one embodiment at least a portion of the protector is spaced inwardly from the inner surface of the jaw.

In one case the protector substantially encloses the tissue engaging feature of the jaw when the jaw is in a closed position.

In one embodiment wherein the protector comprises a shape memory material such as Nitinol.

In one case the protector comprises a loop which extends over the distal tip of the tissue engaging feature.

The loop may define a shaped distal tip. The distal tip of the loop may be rounded.

In one embodiment the protector comprises a wire loop.

In one case a loop extends distally of the distal tip of each jaw to define a grasper.

In one embodiment the protector is movable from a protective configuration extending distal of the tissue engaging feature of a jaw to a retracted configuration in which the tissue engaging feature is exposed.

The protector may be biased into the protective configuration. The biasing may comprise a spring. The protector may be adapted to move into the retracted configuration as the jaws move towards one another.

In another embodiment the protector is integral with the jaw. In this case, the protector may have a profile in the shape of a fin.

In some cases the protector technology described herein may be applied to other suitable instruments having pointed tips.

The invention also provides an instrument comprising:
a pair of jaws which are pivotally movable relative to one another, at least one of the jaws having a pointed distal tip; and
a protector extending from the distal end of the jaw to provide a protective distal tip which is distal of the pointed tip.

In one case the protector comprises a loop which extends over the pointed tip.

In one embodiment the protector comprises a wire loop.

The protector in one case comprises a shape memory material such as Nitinol.

BRIEF DESCRIPTION OF THE DRAWINGS

The invention will be more clearly understood from the following description of some embodiments thereof, given by way of example only, with reference to the accompanying drawings, in which:

FIGS. 1 to 5 are a series of drawings illustrating a protector element and an instrument such as a tenaculum to which the protector element is mounted;

FIG. 6 is an isometric view of another protector element;

FIGS. 11 to 13 are a series of drawings of another tenaculum protector element;

FIGS. 20 to 26 are a series of drawings of a tenaculum according to the invention;

FIGS. 27 to 31 are a series of drawings of a further tenaculum;

FIGS. 46 to 50 are a series of drawings of a further tenaculum;

FIGS. 51 to 53 are a series of drawings of another tenaculum;

FIGS. 58 to 61 are images of another tenaculum according to the invention;

FIG. 62 is an illustration of another tenaculum;

FIGS. 63 to 66 are a series of illustrations of a tenaculum of the invention, in use;

FIGS. 67 to 70 are a series of images of another protector element and associated tenaculum;

FIGS. 71 to 75 are a series of another tenaculum according to the invention;

FIGS. 76 to 78 illustrate various profiles of protector elements;

FIGS. 92 and 93 illustrate an instrument such as a scissors comprising a tip guard.

DETAILED DESCRIPTION

Figure 7:
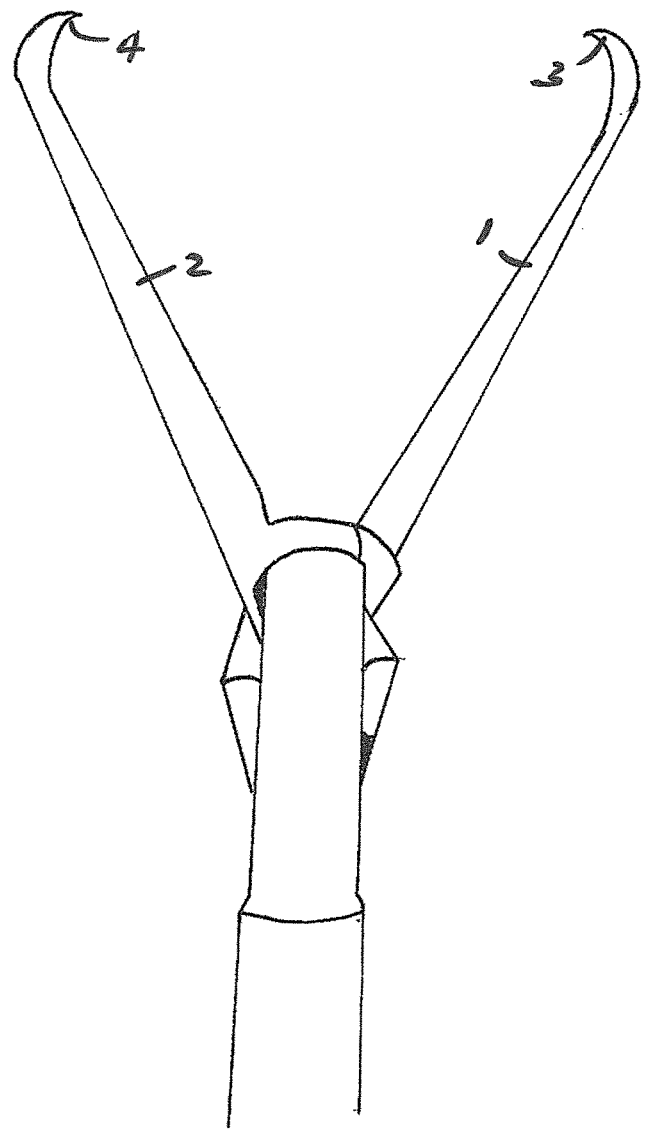
FIGS. 7 to 10 are a series of drawings illustrating another tenaculum protector element.
Figure 8:
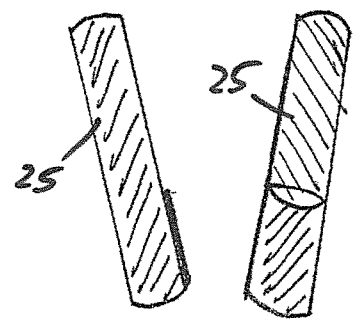
Figure 9:
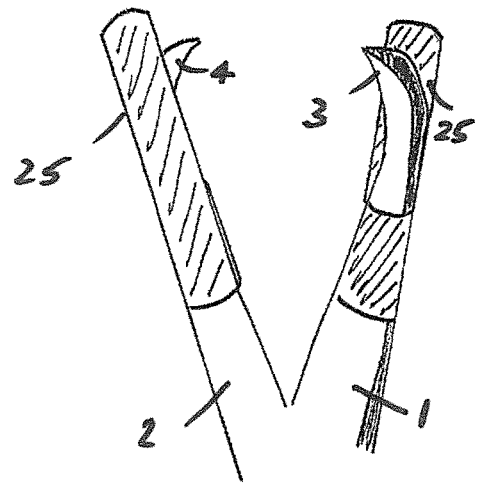
Figure 10:
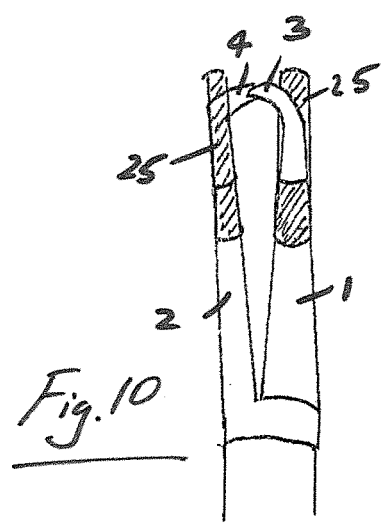
Figure 14:
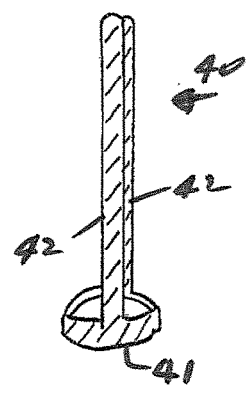
FIGS. 14 to 19 are a series of drawings of a further tenaculum protector element.
Figure 15:
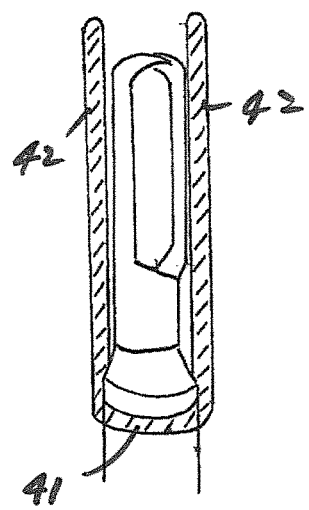
Figure 16:
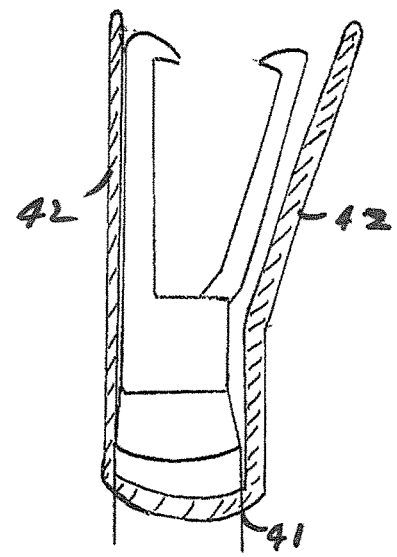
Figure 17:
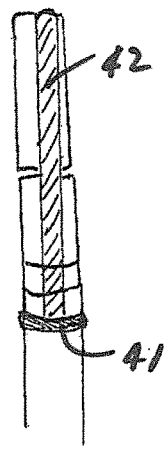
Figure 18:
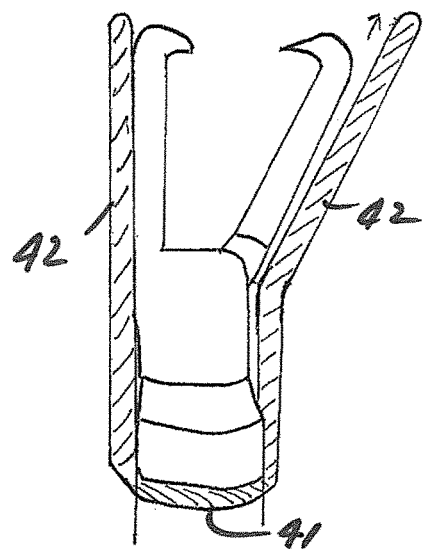
Figure 19:
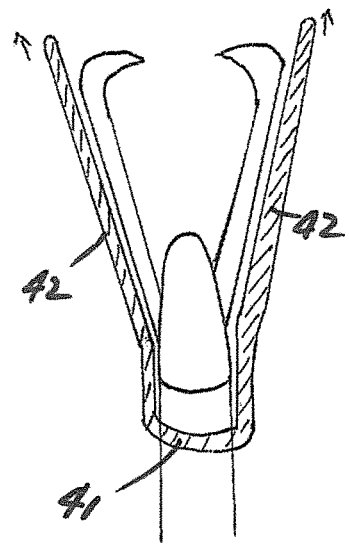

Referring to the drawings there are illustrated various instruments such as tenaculums. In general, the instruments comprise a pair of jaws 1, 2 which are mounted on a shaft for pivotal movement from an open configuration in which the jaws 1, 2 are splayed apart to a closed low profile configuration for example, for delivery and/or retrieval through an access port into an incision or a natural body orifice. The incision or orifice may be retracted to enlarge the access area using devices such as those described in our U.S. Pat. Nos. 6,254,534, 6,846,287 and 7,559,893 the entire contents of the disclosure of each of which are herein incorporated by reference.

In some cases such procedures may be carried out using an inflatable bag such as an artificial pneumoperitoneum bag as described in our U.S. Pat. Nos. 8,920,431, 8,956,286, US 2013/0184536A and WO2014/207077A the entire contents of the disclosure of each of which are herein incorporated by reference. Such procedures in some cases include tissue morcellation.

The jaws 1, 2 each have an engagement feature 3, 4 which may take the form of a spike for engaging tissue.

In the invention, a protector element extends from or is extendable from the distal end of at least one and in most cases both of the jaws 1, 2. The protector element may be a retrofit to a known tenaculum or may form part of a tenaculum. In some cases the protector element is removable/replaceable. At least the tip of the protector element may be at least partially bendable and/or flexible.

Referring to FIGS. 2 to 5, a protector element 10 is illustrated which can be readily releasably mounted to the tenaculum jaws 1, 2. The protector element 10 may be a friction fit, such as an interference fit, with the distal end of the tenaculum jaws 1, 2. The protector 10 in this case has a hole 11 through which the engagement feature 3, 4 extends.

It will be noted that the protector has a distal portion 12, 13 that extends distally from the distal end of the tenaculum jaws 1, 2. This is important as it ensures that the tenaculum has an atraumatic tip which will not harm tissue and will not compromise the integrity of a bag which may be used as a containment device in a procedure.

In FIGS. 2 to 5 there is stretch/slip on the protector which is accommodated and fixed to tenaculum jaws by friction and/or by teeth geometry. Various sizes and numbers of holes/slots for teeth on varying tenaculum may be provided. The protector 10 may be rigid or flexible or a combination of rigid lower and flexible upper.

In some cases a connector may interconnect the protectors 10. The connector may, for example, comprise a tether 20 which may be flexible.

FIG. 6 illustrates tethering together of a pair of protectors 10 to further prevent detachment of either protector during use.

The tenaculum jaws have inner and outer surfaces and the engagement features 3, 4 extend inwardly from the jaws 1, 2. In some cases the protector may primarily engage with the outer surface of the jaws and/or with the inner surface of the jaws.

Referring to FIGS. 7 to 10 individual protectors 25 that only attach to the tenaculum jaws 1, 2 are illustrated. No holes are required to engage with the tenaculum teeth. Friction and/or an engagement feature may be used to retain the protector in place.

In some cases the protector element is movable from a retracted configuration when the tenaculum jaws are closed to a distally extending configuration when the jaws are open.

Referring to FIGS. 11 to 13, in this case a connector 30 between protectors 35 causes the protectors to move as the jaws move. The connector 30 may comprise is a pivoting arm (or similar) mechanism that passively moves the protectors 35 in tandem with operation of tenaculum. The protectors extend upon opening of tenaculum and retract upon closing of tenaculum. There is a greater inherent need for a protector when the tenaculum is open as it poses more of a threat to bag or viscera in this position.

Referring to FIGS. 14 to 19 another movable retrofit protector 40 is illustrated. The protector 40 attaches via a cylindrical band 41 connected to two arms 42. As the tenaculum is opened and closed the protectors 40 respectively extend and contract. The protectors 40 can be narrower or wider than the tenaculum jaws and can widen further towards the distal end of the jaw to offer further lateral protection.

Referring to FIGS. 20 to 26 there is illustrated a tenaculum 50 with a head design including a feature such as a projection 51 to receive an attachable protector 52 via a snap fit/twist fit or similar means. A disposable protector 52 and re-usable tenaculum 50 are provided which facilitates normal tenaculum re-sterilisation in hospitals. The protector 52 can be single or bi-material component that is flexible or rigid or a combination of both. Length can vary and can be produced and supplied in different lengths and geometries.

Referring to FIGS. 27 to 29 another tenaculum 60 is illustrated in which the sharp tooth geometry 61 is offset from the end of the tenaculum jaw. The extension 62 of the jaw can be one rigid part of the jaw itself or be a bonded permanent piece that is rigid or flexible with different material properties.

FIG. 30 illustrates example geometry of a built-in protector 62 which is atraumatic in nature and flexibly offset from sharp tooth geometry 63.

FIG. 31 illustrates a tenaculum 65 which is a one piece single material. Offset teeth 66, 67 can protect a bag or viscera by passively providing a margin of safety and a depth gauge. In other embodiments two levels/secondary offset teeth can accompany primary teeth for extra hold on large pieces of tissue.

Figure 32:
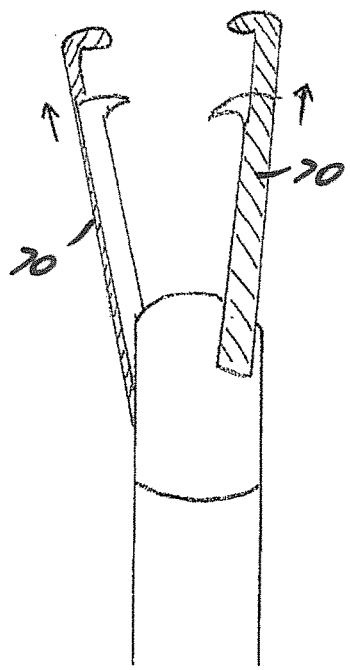
FIGS. 32 to 37 illustrate another tenaculum of the invention.
Figure 33:
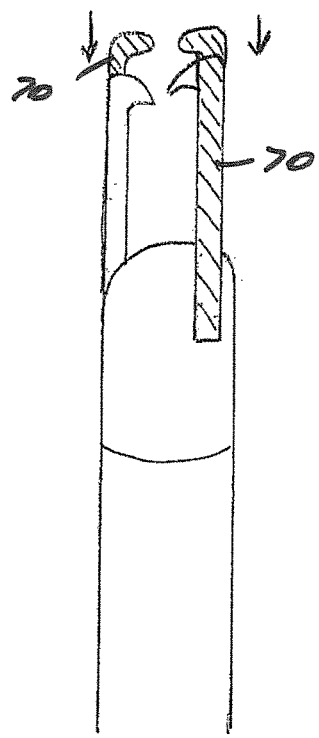
Figure 34:
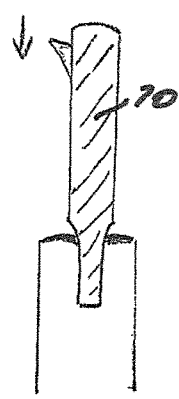

Referring to FIGS. 32 to 34 there is illustrated another protector element 70 which in this case are self-extendable teeth covers. The protectors can be of various geometries and extend and retract automatically upon opening and closing of the tenaculum. This action may be achieved using an internal mechanism which is part of the primary mechanism of the tenaculum. Actuation of the protectors 70 is achieved by the same operation at the handle to achieve grasping with the tenaculum teeth.

Figure 35:
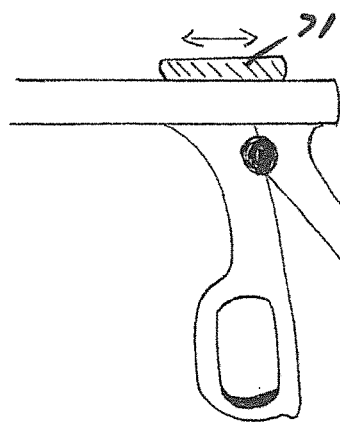
Figure 36:
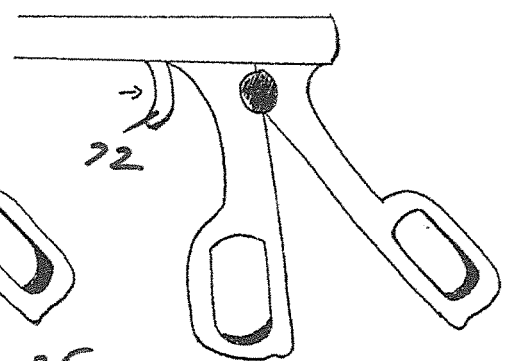
Figure 37:
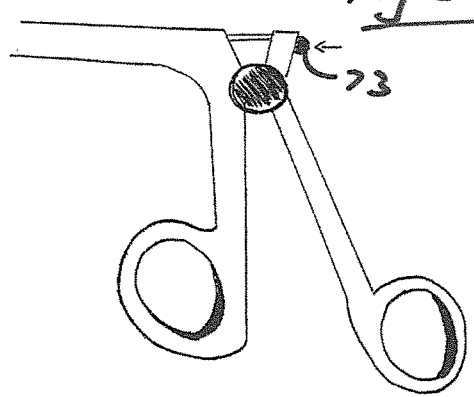

In other embodiments a mechanism to extend and retract built-in protectors can be independently controllable via a handle using a separate control trigger/button or similar. Some alternatives are illustrated in FIGS. 35 to 37—using a slider 71, a trigger 72 or a button 73.

Figure 38:
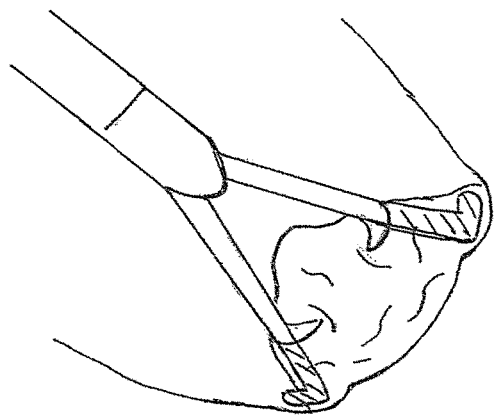
FIGS. 38 to 40 illustrate a tenaculum, in use.

Referring to FIG. 38 the protectors in an extended position can also serve to push undesired bag or tissue away from the sharp teeth of the tenaculum.

Figure 39:
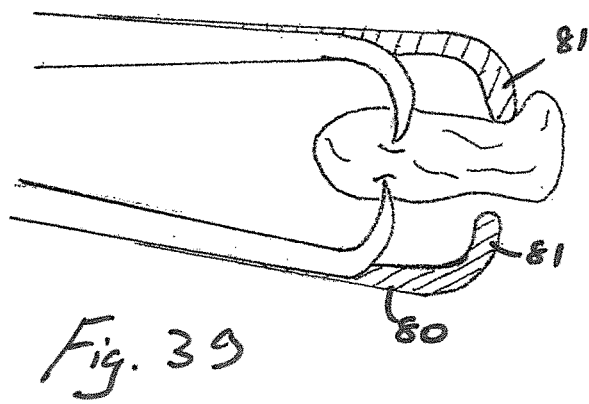
Figure 40:
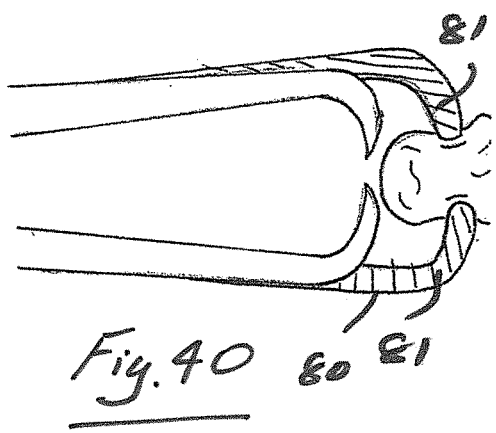
Figure 41:
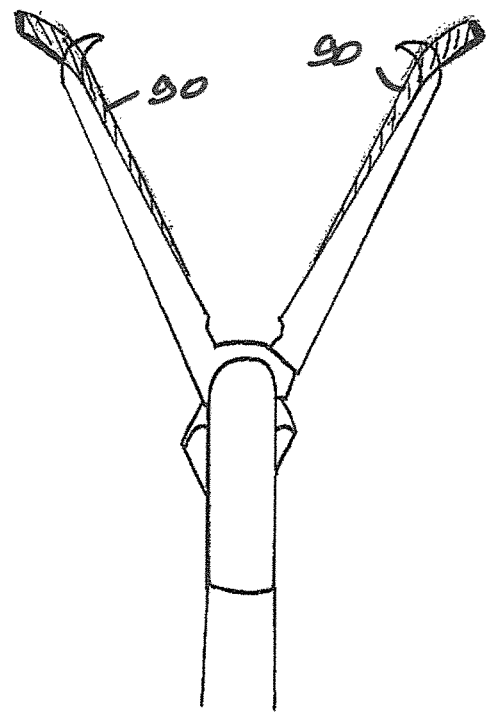
FIGS. 41 to 45 illustrate another tenaculum.
Figure 42:
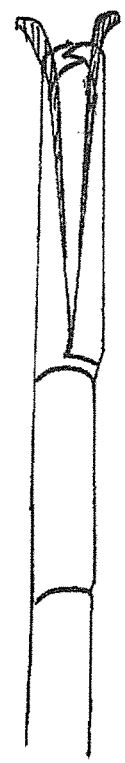
Figure 43:
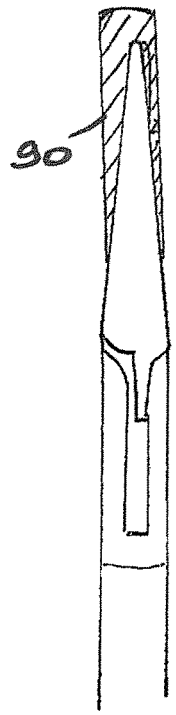
Figure 44:
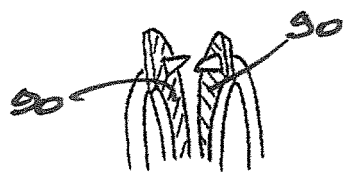

Referring to FIGS. 39 and 40 an extendable protector/guard 80 can have both a passive option/setting in which the protector 80 extends and retracts passively with use of the tenaculum but can also be deactivated or locked in an extended or retracted position at the discretion of the surgeon. When locked in an extended position, the protector 80 can be utilised as an atraumatic graspers with engagement features 81 for the retrieval of smaller tissue fragments if required, with significantly reduced risk to bag or viscera.

In some cases the tenaculum protector may lie on the inner surface of the tenaculum, either mechanically fixed or part thereof. This allows the protector to function without increasing the outer diameter dimensions of the device and therefore not hindering the removal of the device back through a morcellator or port.

Figure 45:
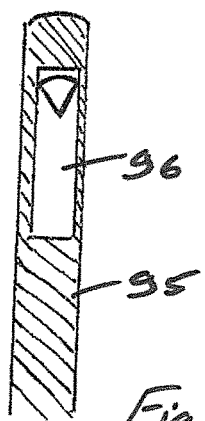
Figure 54:
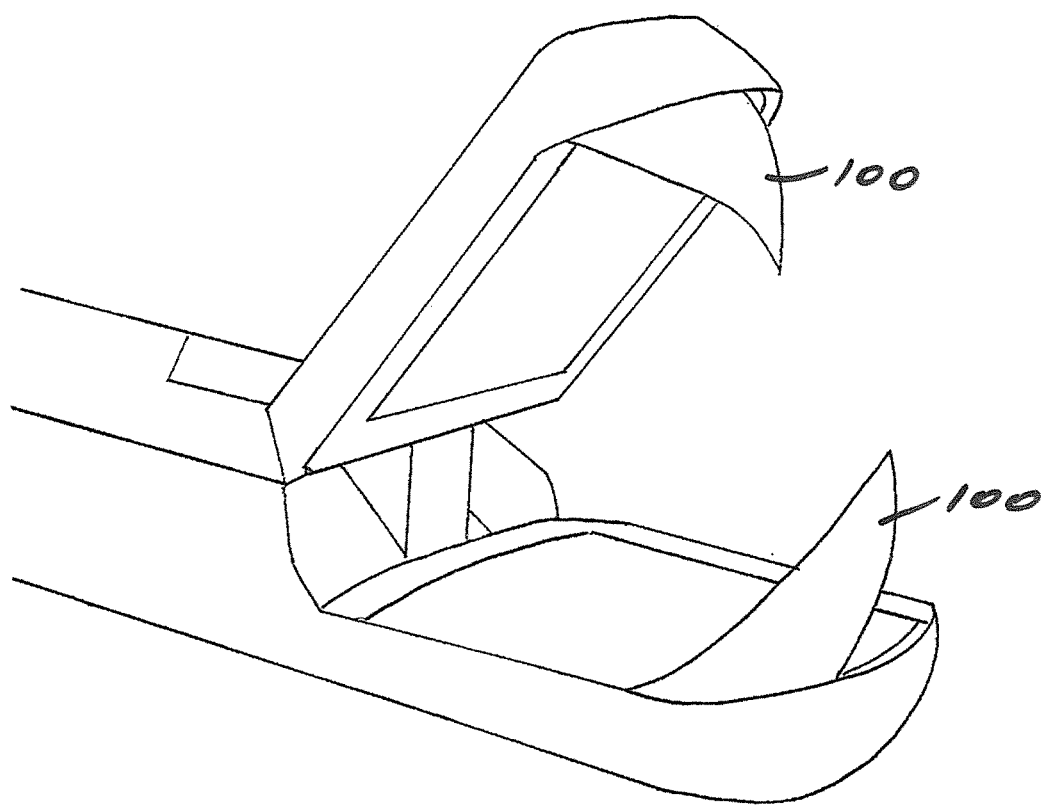
FIGS. 54 to 57 are images of a still further tenaculum.
Figure 55:
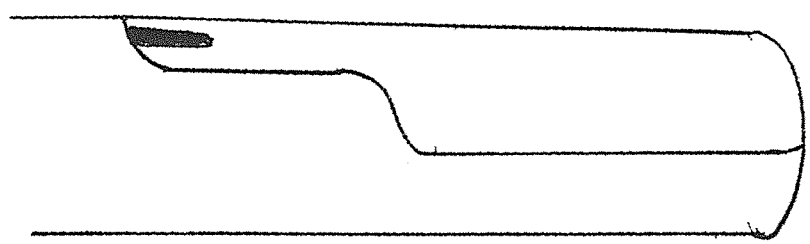
Figure 56:
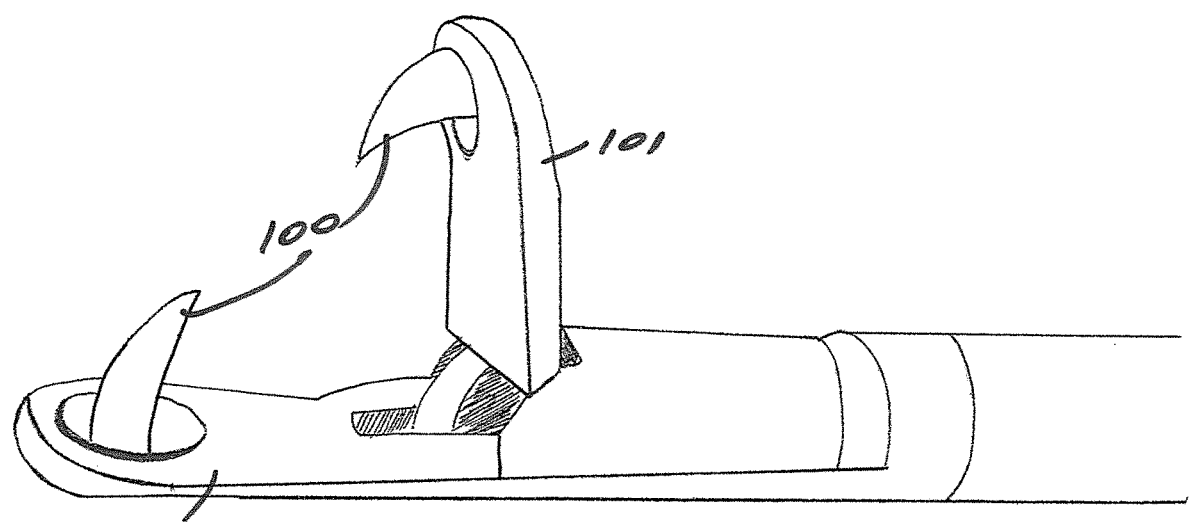
Figure 57:
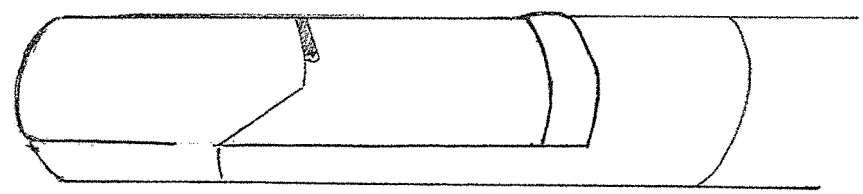

FIGS. 41 to 44 illustrate protectors 90 with these features. The protector 90 includes a slot/hole to accommodate the teeth of the tenaculum. FIG. 45 illustrates a protector 95 with a longer slot 96 to allow for some out-ward flexing when contacting tissue.

In some embodiments the protectors may be both internal of the jaws and separated from the tenaculum jaws.

FIGS. 46 to 50 illustrate various protectors 97 of this type. The protectors 97 may have a local hinging point at the base of the protector or may be connected close to the base of the tenaculum jaw. This offers more flexibility in the protector around larger tissue pieces where risk of damaging bag or surrounding tissue is less severe. The protectors can be supported also by an auxiliary support such as mechanical springs 98 as shown in FIG. 49 to ensure reset to optimum protector position at rest.

Referring to FIGS. 51 to 53 there is illustrated a protector 98 with a grooves and/or channel in which the jaws of the tenaculum slot into, somewhat like a skin. This version may also be retro-fitted.

In some embodiments a tenaculum is provided in which the teeth are completely enclosed/covered when the tenaculum is closed. Teeth offset from tip provides a safer tenaculum.

One such embodiment is illustrated in FIGS. 54 to 57, the tenaculum has offset teeth 100 which are completely enclosed by protectors 101 when the tenaculum is closed.

Referring to FIGS. 58 to 61 there is illustrated a protector 110 comprising an extendable ball 111 and rod 112. A rod 112 with a small spherical shape at its distal tip actuates with activation of the handle/graspers (extends when open, retracts when closed). A rounded (such as spherical) ball 111 is atraumatic and somewhat flexible (can also be rigid). The rounded protector can be an extension of the existing tenaculum mechanism and serves to push bag and/or undesirable tissue away from sharp teeth. Such a protector can also provide haptic feedback to the surgeon to better deliver perception of depth.

Referring to FIG. 62 a protector 120 of the rod and ball type can be combined with an offset tooth arrangement (such as FIGS. 54 to 57) and geometry can be created to home/house the ball upon retraction.

FIGS. 63 and 64 illustrate a protector 130 with a flexible portion while grasping. Haptic feedback is provided through the device and bag material is pushed away from sharp geometry of the tenaculum teeth.

FIGS. 65 and 66 illustrate retraction of the protector 130 upon grasping which clears the mechanism from possible catching on a morcellator or similar device.

Referring to FIGS. 67 to 70 there is illustrated another protector element 120 of the invention which may be releasably mounted to the teeth 121 of a tenaculum 122. The protector element 120 in this case is in the form of a ring which creates a safe circumference around the sharp engagement zone of the tenaculum teeth 121. The protector rings 120 may have features for engagement with the tenaculum teeth or may be a slip-on friction type fit.

Referring to FIGS. 71 to 75 there is illustrated another tenaculum 130 according to the invention which comprises jaws 131, 132 and engagement teeth 133, 134. In this case the teeth 133, 134 are movable from an extended position near the distal tip of the jaws 131, 132 when the jaws of the tenaculum are closed to a retracted position more proximal of the distal tip when the jaws open. In this case the protector provided by or on the distal tip of the jaws remains fixed and the teeth 133, 134 move-up when closing, down and away from the distal tip when open. This protects viscera and/or a containment bag when the tenaculum is in use.

FIGS. 76 to 78 illustrate different geometries for a tenaculum protector element 140, 141 in which the protection zone is widened distally.

Figure 79:
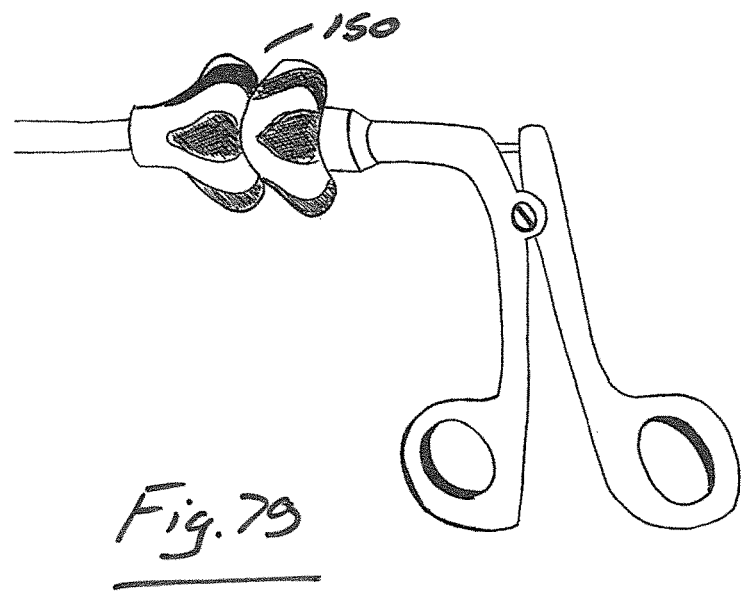
FIGS. 79 and 80 illustrate one activation system of a tenaculum of the invention.
Figure 80:
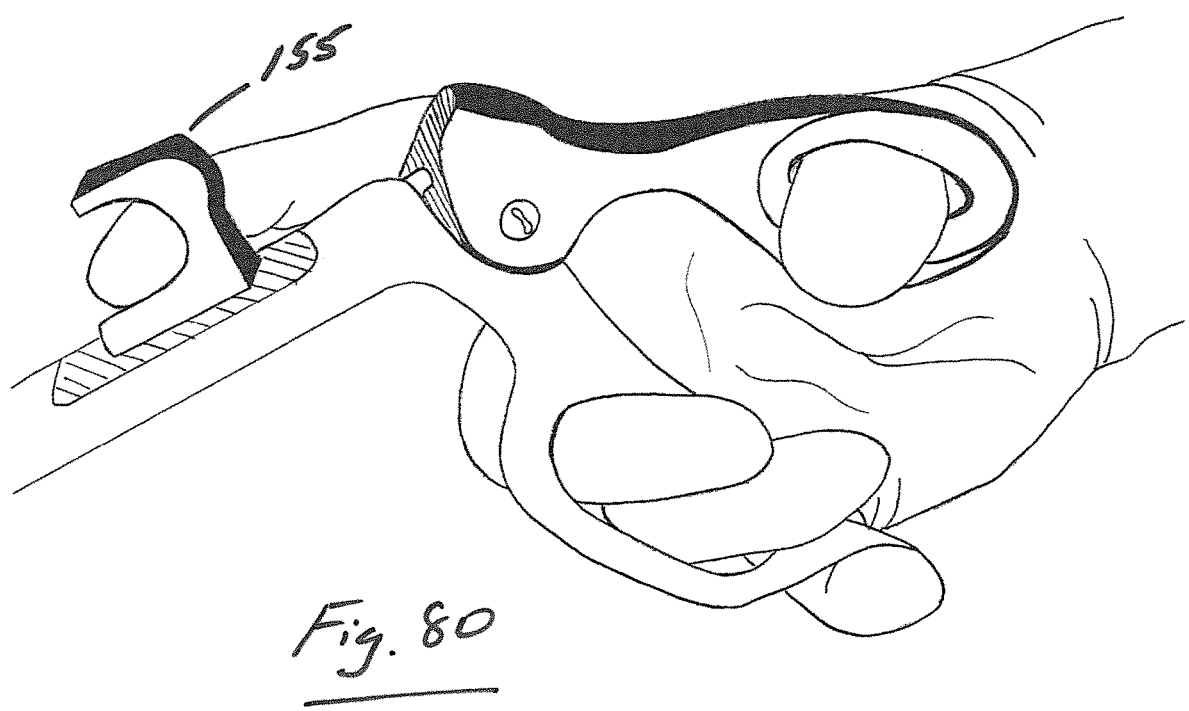

FIGS. 79 and 80 illustrate some activation methods for activating movable protector elements. In FIG. 79 a secondary twisting component 150 may be used to activate the moving protector elements. FIG. 80 illustrates an additional trigger 155 which may be used to activate the protector elements. Such mechanisms may also be used for activing movable tenaculum teeth.

In any of the embodiments of the invention the protector may be of a shape memory material such as Nitinol.

Referring to FIGS. 81 to 84 there is illustrated an instrument such as a tenaculum which comprises a loop 200 which extends over the distal tip of the tissue engaging features 201 at the distal ends of the jaws 202, 203. The loop defines a shaped distal tip which may be rounded to provide a smooth profile. The loop 200 extends distally of and also surrounds the tissue engaging feature 201. In effect, the loop circumscribes the tissue engaging feature.

In this case the loop is of wire and may, for example, be of spring metal such as steel. Preferably the loop is of a shape memory material such as Nitinol which ensures that the wire will always return to the starting position regardless of how many times it is bent out of the way. The halo shaped wire 200 can be close to the tissue engaging feature 201 or may extend distally away from it.

Figure 81:
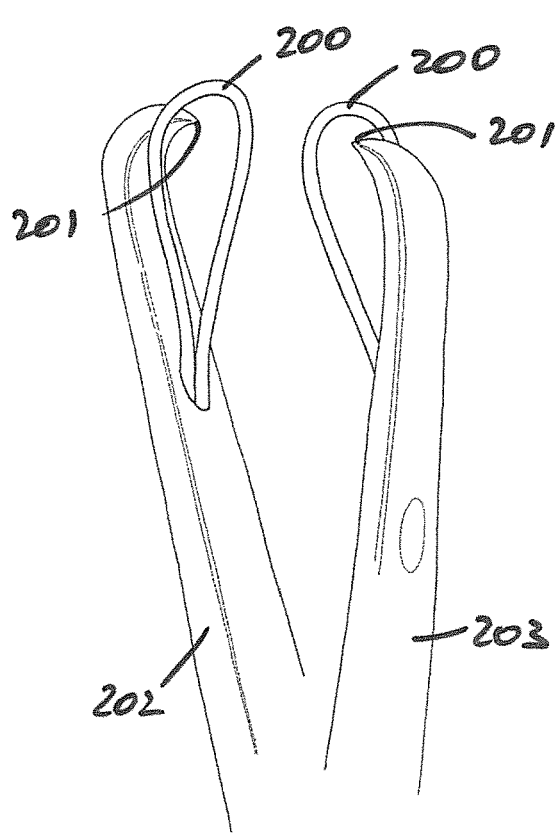
FIGS. 81 to 84 are illustrations of another tenaculum according to the invention.
Figure 82:
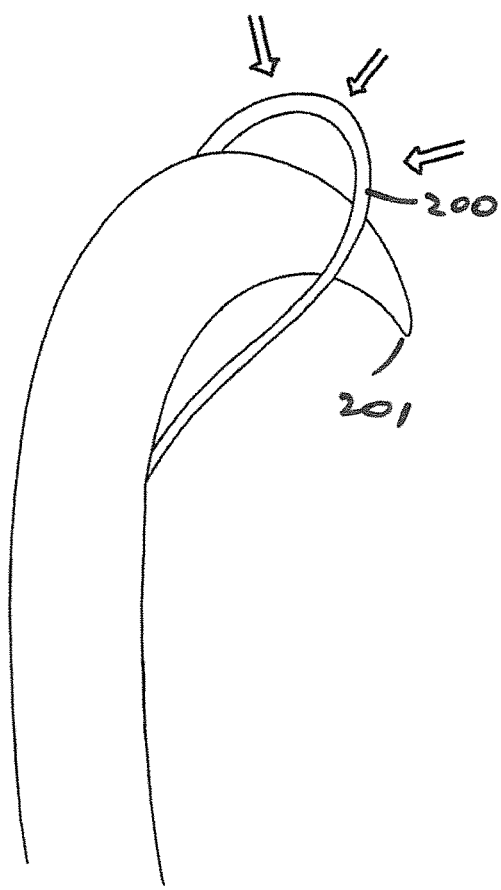
Figure 83:
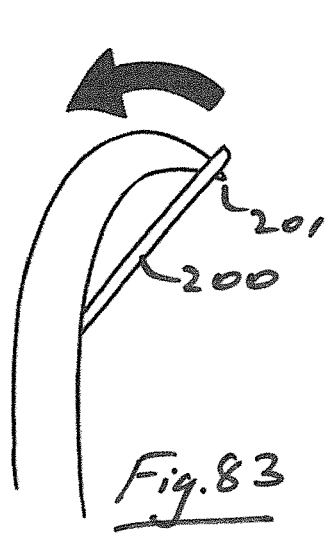
Figure 84:
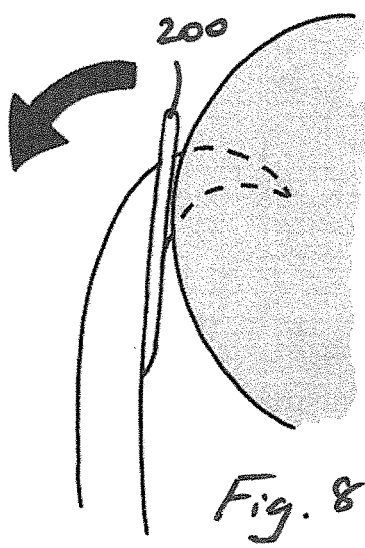

The wire loop 200 is in this case set in a straight configuration which, when shaped into a loop has the effect of biasing the wire into the protective configuration illustrated in FIG. 81. This biasing is important in retaining the loop in the protective configuration, in use.

Figure 85:
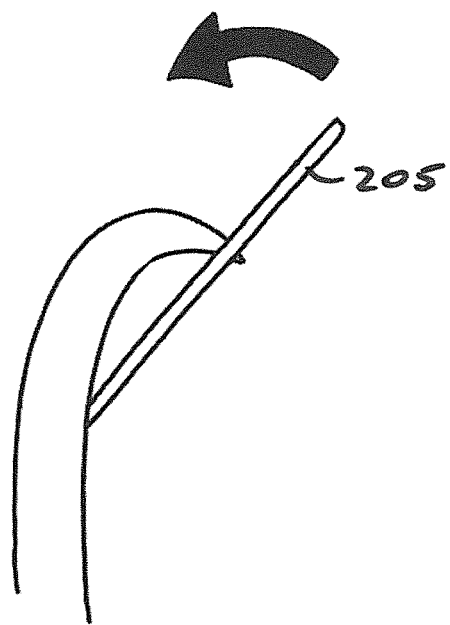
FIG. 85 illustrates another tenaculum of the invention.
Figure 86A:
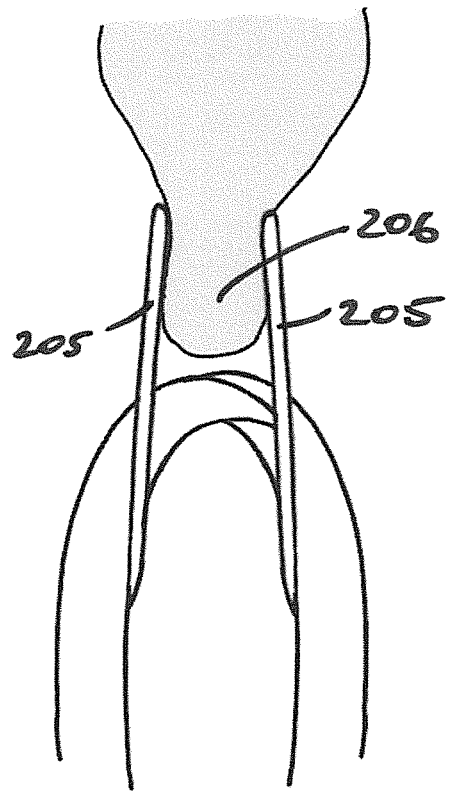
FIG. 86(a) illustrates the tenaculum of FIG. 85 in one mode of use.
Figure 86B:
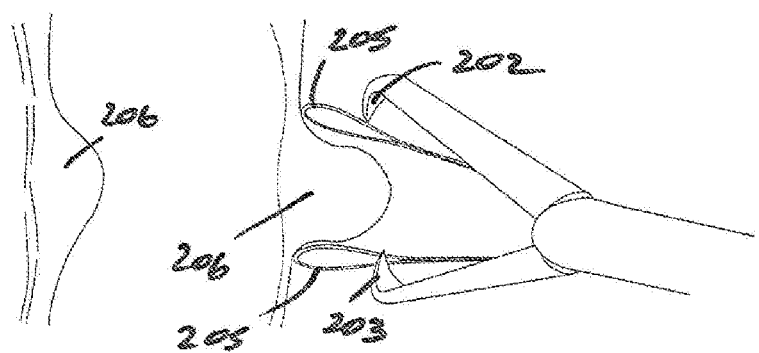
FIGS. 86(b) to 86(e) illustrate the tenaculum of FIG. 86 in use.
Figure 86C:
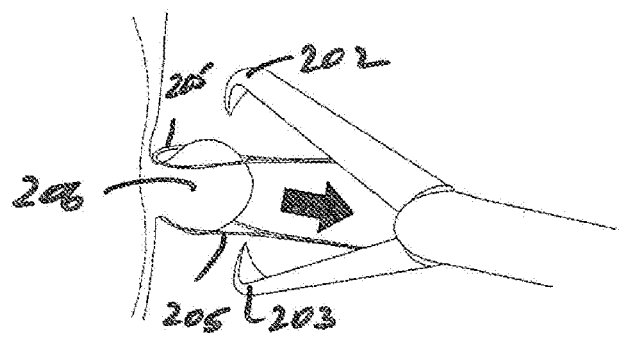
Figure 86D:
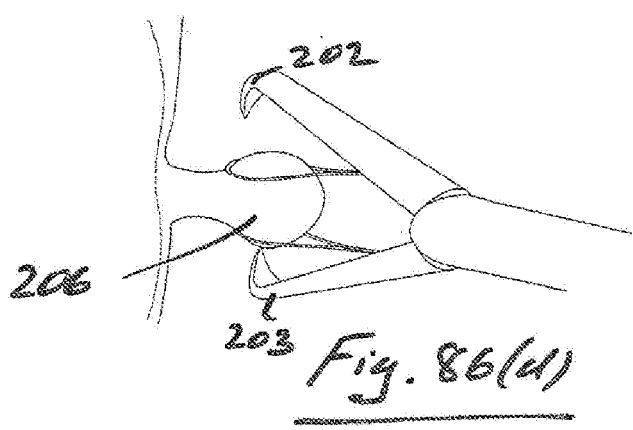
Figure 86E:
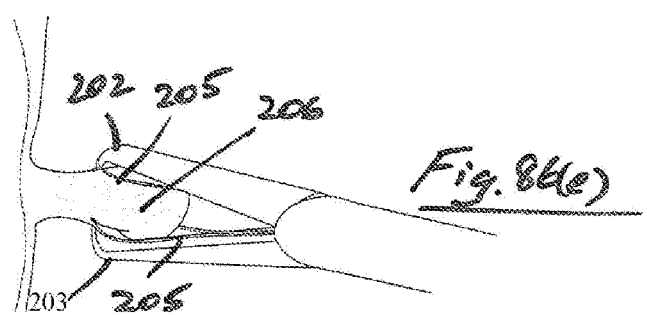

Referring to FIGS. 85 and 86(a) to (e), in this case a wire loop 205 of the type described with reference to FIGS. 81 to 84 is illustrated being used as a grasper for grabbing soft tissue 206. Referring to FIGS. 86(b) to (e) the protector loops 205 extend distally beyond the jaws 202, 203 and may be activated, for example, by activating a switch at the proximal end of the instrument to engage a specimen 206. The loops 205 may then be pulled proximally to pull the specimen 206 to the tissue engaging features 201 as illustrated in FIGS. 86(c) and (d). the jaws 202, 205 of the end effector (scissors, tenaculum or grasper) may then be activated to firmly and efficiently engage the specimen 206.

There is an individual loop for the or each jaw. This ensures that the individual loops respond independently to movement of the jaw to which they are coupled. Each loop forms a halo around the tissue engaging feature of the jaw to which it is coupled. This halo is maintained as the jaw opens and closes but does not impede the operation of the device. In use, it is important that the tissue engaging features at the distal end of the device can engage with tissue without obstruction and without pushing the desired tissue away from the device. This ensures the efficient operation of the device in gripping tissue.

The instruments illustrated may comprise tissue engaging features such as spikes at the distal end of one or both jaws. Such spikes facilitate a firm engagement with tissue, especially hard tissue such as a fibroid or stone. There may be a single spike at the distal end of each jaw which is especially suitable for applying a single large localised gripping force on hard tissue. For softer tissue there may be more than one spike at the distal end of at least one of the jaws. Such additional spikes are usually arranged across the jaw at the distal end.

The device of FIGS. 85 and 86 is particularly suitable for manipulating certain types of tissue such as softer tissue as the distally extending loops may be used to easily grip tissue and, on retraction, deliver it to the spiked tissue engaging features of the jaws for further manipulation.

Figures 87, 88:
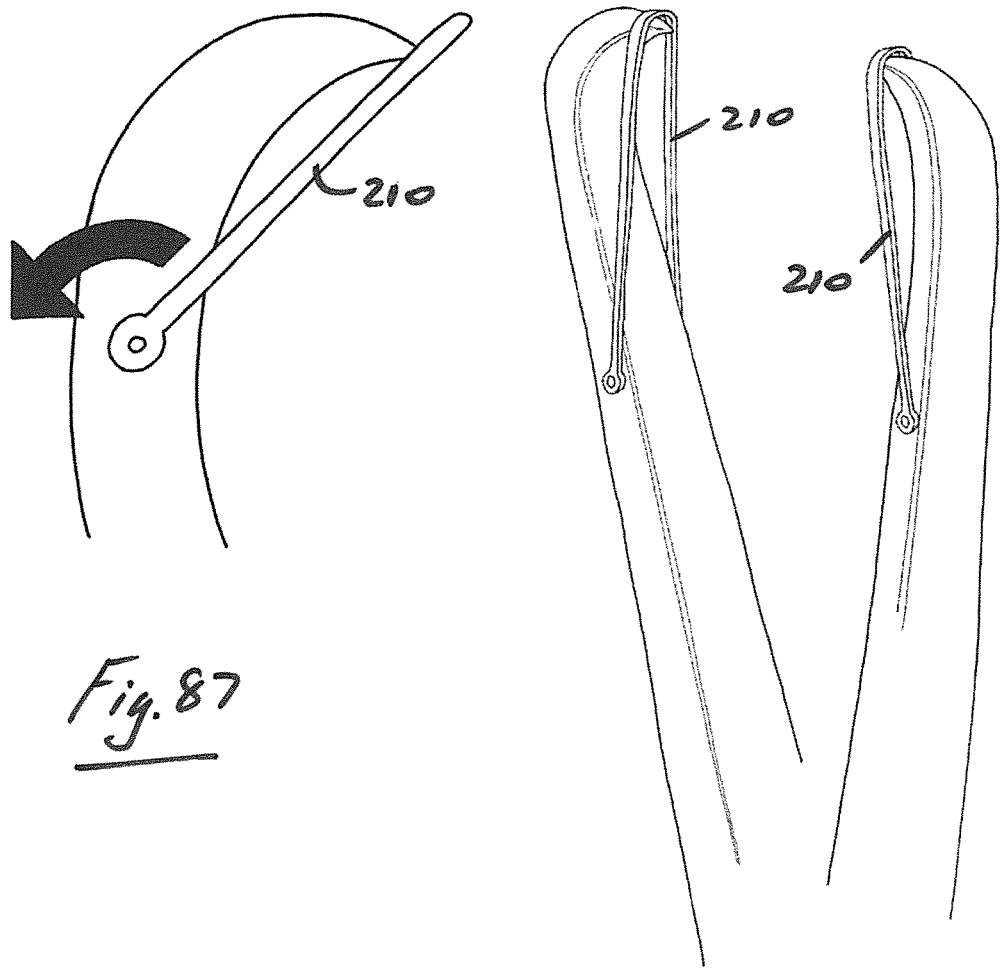
FIGS. 87 and 88 illustrate a further tenaculum with a tip guard.

Referring to FIGS. 87 and 88, in this case the protector comprises a wire loop 210 that may be spring biased into the protective position illustrated and which is automatically moved away as the tissue engaging features engage with tissue. Again, the protective loop surrounds the tip to prevent damage to a tissue containment bag or the like.

Figure 89:
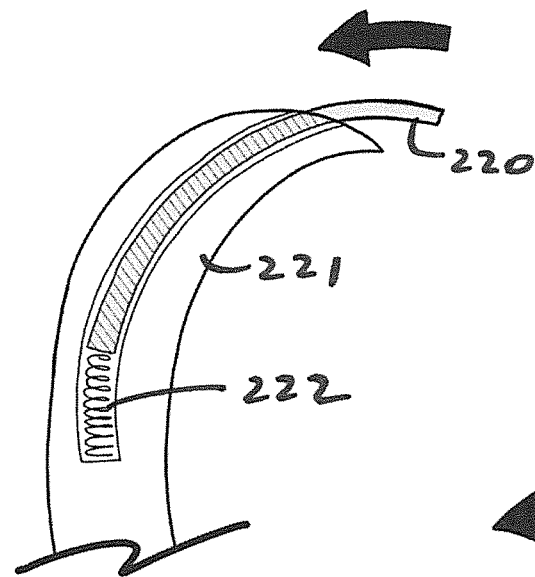
FIG. 89 is a view of another tenaculum with a spring loaded tip guard.

Referring to FIG. 89, in this case a protector 220 normally extends distally from the tip of the jaw 221 under the biasing of spring 222. In operation of the tenaculum the protector is retracted but returns to the protective position under the biasing of the spring 222.

Figure 90:
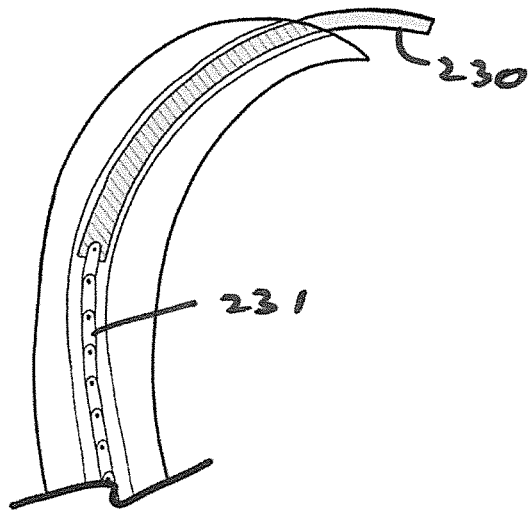
FIG. 90 is a view of a further tenaculum.

Referring to FIG. 90, in this case a protector 230 is moved as the jaws of the tenaculum are closed using a linkage mechanism 231. Thus, the protector 230 retracts as the jaws of the tenaculum are closed and the tissue is engaged by the tissue engaging features of the jaws.

Figure 91:
FIG. 91 is a view of another tenaculum with an integral tip guard.

FIG. 91 illustrates a tenaculum with an integral protector 240 which extends distally of the tissue engaging feature 241. The protector 240 is fin-shaped to avoid damage to a tissue collecting bag.

In some cases the protector technology described herein may be applied to other suitable instruments having pointed tips. Examples of such instruments include a forceps, a grasper or scissors. For example, and referring to FIGS. 92 and 93, a protector loop 250 such as those described alone may be provided for the pointed tip 251 of a scissors 252.

In some cases, such as those described above an artificial pneumoperitoneum bag is used which provides space and vision.

In other cases a bag is used for a tissue such as, for example, a uterus that is brought to the surface of the incision or body orifice without space or vision. In such cases the tenaculum of the invention with the protector distal tip can also be inserted to aid tissue removal without the risk of damaging the bag or surrounding tissue. Indeed, in some cases, the tenaculum of the invention can be used to group target tissue without the need for a bag, wherein the protector safety extension prevents grabbing of normal tissue in the region of the tissue to be removed.

The invention is not limited to the embodiments hereinbefore described, which may be varied in construction and detail.

The invention claimed is:
1. An instrument comprising:
a first jaw and a second jaw, the first jaw being pivotally connected to the second jaw,
at least the first jaw having at least one pointed member at or adjacent to a distal end of the first jaw; and a first protective element connected directly to the first jaw and extending from a position proximal of a distalmost end of the first jaw to a position distal of the distalmost end of the first jaw in a first position of the first protective element, wherein the distal end of the first jaw is spaced apart from the first protective element when the first jaw and the second jaw are in an open configuration, wherein the first protective element moves relative to the first jaw when the first jaw moves between the open configuration and a closed configuration of the first jaw and the second jaw.

2. The instrument of claim 1, wherein the second jaw has at least one pointed member at or adjacent to a distal end of the second jaw, and wherein a second protective element extends distally of the distalmost end of the second jaw, wherein the at least one pointed member of the second jaw is spaced apart from the second protective element when the first jaw and the second jaw are in the open configuration.

3. The instrument of claim 2, wherein the first protective element and the second protective element are configured to contact each other as the instrument moves from the open configuration to the closed configuration.

4. The instrument of claim 3, wherein the at least one pointed member of the first jaw and the at least one pointed member of the second jaw are configured to contact each other in the closed configuration.

5. The instrument of claim 1, wherein the first protective element comprises a loop which circumscribes the at least one pointed member of the first jaw when the first jaw and the second jaw are in the closed configuration.

6. The instrument as claimed in claim 1, wherein the at least one pointed member is a tissue grasper having one or more pointed elements.

7. The instrument of claim 1, wherein an entirety of the first protective element is proximal to the at least one pointed member of the first jaw in a second position of the first protective element, the second position different from the first position.

8. The instrument of claim 1, wherein the first jaw includes an opening proximal to the at least one pointed member, and wherein the first protective element protrudes through the opening.

9. The instrument of claim 1, wherein the at least one pointed member is angled toward a longitudinal axis of the instrument relative to the first jaw.

10. The instrument of claim 1, wherein the first protective element includes a shape memory material, and wherein the first protective element is biased away from the at least one pointed member of the first jaw.

11. An instrument comprising:
a pair of jaws which are pivotally connected to each other, at least a first jaw of the pair of jaws having only one pointed distal tip; and
a protector extending from the first jaw from a position proximal of a distalmost end of the pointed distal tip to a position distal of the distalmost end of the first jaw in a first position of the protector, wherein the protector is spaced apart from a distal end of the first jaw,
wherein an entirety of the protector is proximal to the pointed distal tip of the first jaw in a second position of the protector, the second position different from the first position.

12. The instrument of claim 11, wherein the protector comprises a loop which is configured to circumscribe the pointed distal tip when the instrument is in a closed configuration.

13. The instrument of claim 11, wherein the protector comprises a shape memory material.

14. The instrument of claim 11, wherein the first jaw includes an opening proximal of the pointed distal tip, and wherein the protector protrudes through the opening.

15. The instrument of claim 11, wherein the pointed distal tip is angled toward a longitudinal axis of the instrument relative to the first jaw.

16. The instrument of claim 11, wherein the pointed distal tip is a tissue grasper.

17. An instrument comprising:
a pair of jaws pivotally connected together, wherein at least a first jaw from the pair of jaws includes a grasping member; and
a loop extending from the first jaw,
wherein the grasping member extends through the loop in a first configuration such that a portion of the grasping member is disposed closer to a longitudinal axis of the instrument than the loop, and
wherein the loop is positioned closer to the longitudinal axis than the portion of the grasping member in a second configuration.

18. The instrument of claim 17, wherein the loop circumscribes the grasping member in the second configuration.

19. The instrument of claim 17, wherein the grasping member is located at a distal end of the first jaw, and the grasping member is a tissue grasper having one or more pointed elements.

20. The instrument of claim 17, wherein a second jaw from the pair of jaws includes a grasping member, wherein a loop extends from the second jaw, and wherein the loop extending from the first jaw and the loop extending from the second jaw are configured to contact each other in the second configuration.

* * * * *